United States Patent [19]

Cooper et al.

[11] Patent Number: 5,442,435
[45] Date of Patent: Aug. 15, 1995

[54] FLUID COMPOSITION SENSOR USING REFLECTED OR REFRACTED LIGHT MONITORING

[75] Inventors: Stephen R. W. Cooper, Tustin; Guangyu Zhang, Grand Rapids, both of Mich.

[73] Assignee: Nartron Corporation, Reed City, Mich.

[21] Appl. No.: 217,611

[22] Filed: Mar. 24, 1994

[51] Int. Cl.$^6$ ............................................. G01N 21/41
[52] U.S. Cl. ................................... 356/133; 356/136; 73/30.04; 73/705
[58] Field of Search ............... 356/128, 133, 135, 136, 356/137; 73/30.01, 30.02, 30.04, 705

[56] References Cited

U.S. PATENT DOCUMENTS

| | | | |
|---|---|---|---|
| 3,056,297 | 10/1962 | Duke | 356/133 |
| 3,311,014 | 3/1967 | Klitt et al. | 356/133 |
| 3,932,038 | 1/1976 | Schweizer et al. | 356/133 |
| 4,306,805 | 12/1981 | Arrington | 356/133 |

FOREIGN PATENT DOCUMENTS

| | | | |
|---|---|---|---|
| 90032 | 5/1984 | Japan | 356/136 |
| 38634 | 2/1989 | Japan | 356/136 |
| 170838 | 7/1989 | Japan | 356/136 |

OTHER PUBLICATIONS

"Data Book" Optek Technology, Inc., 1989, 1990, pp. 17–20.
Ward's Auto World Magazine—May 1994, 2 pages.

Primary Examiner—F. L. Evans
Attorney, Agent, or Firm—Watts, Hoffman, Fisher & Heinke

[57] ABSTRACT

A gas density sensor having a prism in contact with a fluid whose density is determined. A light source shines light into the prism. The light is reflected off prism surfaces in contact with the fluid. As the fluid density changes, the amount of light reflecting off these surfaces changes depending upon fluid density. A detector placed to receive light reflecting off the surfaces determines density from sensed light.

16 Claims, 17 Drawing Sheets

FLUID COMPOSITION SENSOR USING REFLECTED OR REFRACTED LIGHT MONITORING

FIELD OF THE INVENTION

The present invention concerns method and apparatus for measuring fluid properties such as gas density, gas or liquid chemical composition, physical state, temperature, or pressure.

BACKGROUND ART

This invention concerns a method of directly measuring a physical property of a fluid such as gas density and/or using the measured physical property to determine another property such as gas pressure. Conventionally, gas density can be determined by weighing a gas container, measuring its volume and subtracting the container's empty weight. The weight difference is then divided by the container's volume to obtain the density. A major difficulty resides in trying to measure the filled container's weight, especially when the container is mounted for use. Gas density can also be determined by applying gas law data to a measured pressure. This requires an accurate pressure and temperature measurement, and an accurate determination of the gas law for the measured gas. The gas law in turn will vary from gas to gas and at different combinations of pressure, density and temperature.

Gas pressure measurement also presents challenges. At the present time, one of the most common methods of gas pressure measurement is the Bourdon Tube. This simply consists of a bent or coiled tube closed at one end with the other end open and mechanically fixed to the system whose gas pressure is to be measured. The outside of the tube is kept at a reference pressure (usually atmosphere). When the pressure inside the tube exceeds the pressure outside the tube, the tube will began to straighten. When the pressure inside falls, the tube will began to return to its bent form. Typically, a device such as a hinged meter needle, is attached to the closed end of the Bourdon tube. As the tube moves the needle then moves along the meter scale. By appropriate choice of materials and tube dimensions, it is possible to achieve a meter indication that is approximately linear or at least smoothly varying with respect to pressure variation. The disadvantages of the Bourdon tube reside in the difficulty of repeatably reproducing the same mechanical behavior from tube to tube. This results in a need to either mechanically calibrate each tube or accept a large variation in pressure response from tube to tube. The motion of the tube is also susceptible to temperature variation. As the tube heats its thermal expansion will cause extension and its other mechanical properties will also vary. Additionally, a mechanical linkage is required to whatever is used as a meter. Mechanical linkages necessarily exhibit hysteresis, wear and 'play'.

Another common measuring technique is to place a strain gauge on a diaphragm. Strain gauges can be composed of materials such resistive films or piezoelectric elements, among others. The diaphragm in turn is fixed at the edges and is placed between the pressure to be measured and a reference pressure. As the pressure difference between the measured and reference sides of the diaphragm varies, the diaphragm will flex towards or away from the reference pressure. This flexing results in strain applied to the strain gauge which in turn provides an electrically measurable indication of the degree of strain. The degree of strain is then hopefully proportional to the pressure difference. Strain gauge pressure measurement has the advantage of providing a direct electrical signal that can be readily monitored by automatic equipment such as computers or controllers. Strain gauge meters can also be made much smaller than Bourdon tube devices and can even be micromachined into integrated circuit wafers. Disadvantages include temperature induced variation in response, poor unit to unit repeatability and high cost.

Optek Technology, Inc. of West Crosby Road, Carrollton, Tex. 75006 has a published data book (copyright 1989, 1990) that indicates its OPB model XXX series sensors can be used to sense the absence or presence of a liquid. FIG. 5 of *Optek Application Bulletin* 204 (July 1989) notes that light signal variations due to reflection at an interface between a liquid and a transparent material can be used to detect the presence of a liquid.

In laboratory settings it is possible to indirectly determine gas density or pressure by monitoring variations in the speed of sound or speed of light in the gas. However, until now this has not translated into a low cost, practical and readily employable device outside the lab.

DESCRIPTION OF THE PRESENT INVENTION

The present invention utilizes a variation in index of refraction (ratio of light speeds) with respect to a chemical or physical property of a fluid. This variation is exploited by placing a refracting and/or reflective device such as a prism in a light path so that the light reflects from an interface between the reflective device and a fluid whose chemical or physical property is to be measured. The amount of light refracted or reflected varies as the index of refraction of the fluid in contact with the device varies. This variation in light can then be measured by devices such as photodiodes or photocells and used to determine the chemical or physical property.

Apparatus constructed in accordance with a preferred embodiment of the invention monitors a density of a gas contained within a vessel. The vessel includes a gas port for putting gas into the vessel and at least one optics port for allowing radiation to enter the vessel. A multi-sided radiation transmissive prism is supported within the vessel to intercept radiation entering the vessel and includes first and second reflecting surfaces at an interface between the gas and the radiation transmissive prism. A radiation source directs a beam of radiation into the vessel through the optics port to the radiation transmissive prism along a path that causes the radiation to strike a first reflecting surface at a controlled angle and then reflect off the first reflecting surface and pass through the prism to the second reflecting surface. A detector monitors radiation intensity after the radiation reflects off the second reflecting surface and provides an indication of gas density based upon an output from the detector.

Challenges include locating cost effective and temperature stable light sources and light measuring devices as well as designing and building optical components that are sensitive to small variations in index of refraction. These and other challenges are overcome in the preferred embodiment of the present invention which is described in greater detail below in conjunction with the accompanying drawings.

BEST MODE FOR PRACTICING THE INVENTION

Figure 1:
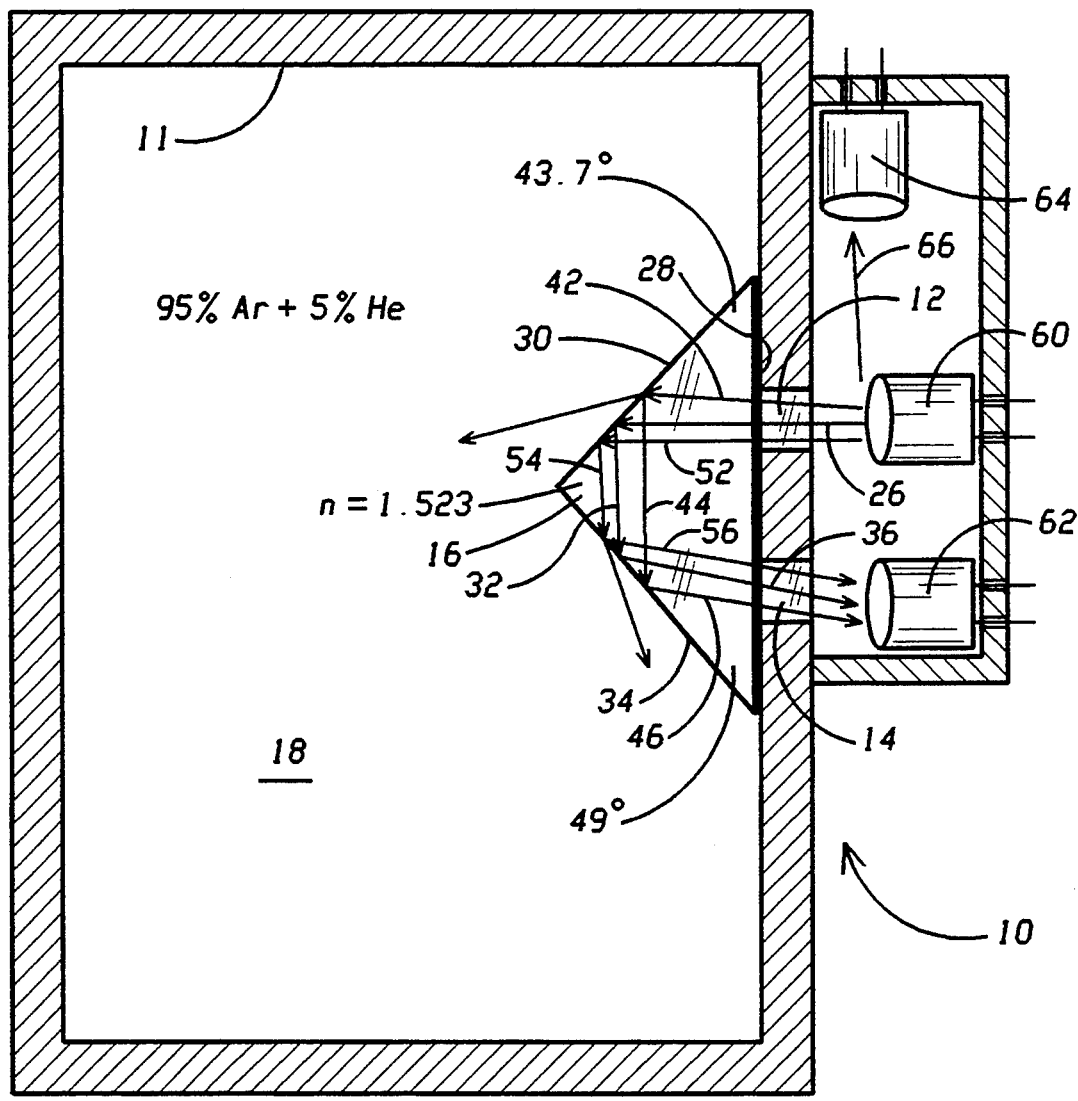
FIG. 1 is a schematic depiction of a gas density sensor constructed in accordance with the present invention.

The physical principle behind the invention comes from the Clausius Mossiti Relation.

$$\frac{\epsilon - 1}{\epsilon - 2} = \alpha \cdot \text{density} \qquad \text{Eq. (1)}$$

For instance, in Argon the standard temperature and pressure density is $1.7832 \times 10^{-6}$ g/cm$^3$ and the STP permitivity is 1.000517. This gives a value of 0.097 for alpha. Equation 1 implies that the permitivity of a gas arises primarily from the individual dipole moments of the constituent molecules. As a result, the greater the density of the gas, the greater the number of dipoles (molecules) in a given volume of gas which increases the value of the permitivity. In the appropriate units the permitivity is given by equation 2.

$$\epsilon = 1 + X \qquad \text{Eq. (2)}$$

Equation 3 for electric susceptibility as a function of density is then obtained from equations 1 and 2.

$$\frac{X}{X + 3} = \alpha \cdot \text{density} \qquad \text{Eq. (3)}$$

If the susceptibility (X) is small, one can apply the binomial expansion to equation 3 expand the denominator. If the susceptibility is less than 0.01 one can truncate to only linear terms and obtain the following:

$$X \cdot \left( \frac{1}{3} + \frac{X}{3^2} \right) = \alpha \cdot \text{density} \qquad \text{Eq. (4)}$$

Keeping only the first order term one has equation 5.

$$\frac{X}{3} = \alpha \cdot \text{density} \qquad \text{Eq. (5)}$$

Substituting the definition of susceptibility from equation 2 the relation becomes $$\epsilon = 1 + 3 \cdot \alpha \cdot \text{density} \qquad \text{Eq. (6)}$$

This implies that for gasses with a permitivity no greater than 1.01, the permitivity ($\epsilon$) will vary linearly with density to 99% or better. For most if not all gasses the relationship between susceptibility and the index of refraction n for the gas is:

$$n = \sqrt{\epsilon} \qquad \text{Eq. (7)}$$

Substituting for the susceptibility and using the binomial expansion (first 3 terms) the following is obtained:

$$n = 1 + \frac{X}{2} - \frac{1}{4} \cdot \frac{X^2}{2} \qquad \text{Eq. (8)}$$

For small susceptibilities the non linear term can be dropped to obtain:

$$n = 1 + \frac{3}{2} \cdot \alpha \cdot \text{density} \qquad \text{Eq. (9)}$$

This shows that the index of refraction n will be linear to better than 98% for susceptibilities <0.01. Snell's Law states that for two media with indexes of refraction of n1 and n2, respectively:

$$n1 \cdot \sin(\theta_1) = n2 \cdot \sin(\theta_2) \qquad \text{Eq. (10)}$$

In this relation, the angles are measured relative to the normal to the interface between the two media and indicate the trajectory a light ray will follow in going from one media to the next. For n1>n2, it is possible to set the angle $\ominus 2$ to 90 degrees to obtain the critical angle:

$$n_1 \sin\theta_1 = n_2 \qquad \text{Eq. (11)}$$

Substituting for n2 from equation 10 the variation in critical angle with respect to gas density is shown as:

$$\theta_1 = \arcsin \frac{(1 + 3/2 \cdot \alpha \cdot \text{density})}{n_1} \qquad \text{Eq. (12)}$$

When the density term is sufficiently small, the critical angle will vary approximately linearly with density.

At angles less than the critical angle, partial reflection will occur. The vector component of light polarized perpendicular to the plane of the incident, reflected and refracted rays, can be determined as can the vector component of light polarized coplanar with the incident, reflected and refracted rays. With $n_g$ being the index of refraction of the gas, the fraction of co-planar polarization light is given by equation 13:

$$\text{refl}_{par} = \frac{n^2 \cdot \cos(\theta) - n\sqrt{n_g^2 - n^2 \sin(\theta)^2}}{n^2 \cdot \cos(\theta) + n\sqrt{n_g^2 - n^2 \sin(\theta)^2}}, \qquad \text{Eq. (13)}$$

Where n is the index of refraction on the incident media.

For a non-polarized light source, an approximately equal mixture of co-planar and perpendicular components can be expected, this results in an average reflected to incident power ratio as given by equation 14:

$$\text{refl}_{total} = \frac{\frac{n_g^2 \cos(\theta) - n\sqrt{n_g^2 - n^2 \sin(\theta)^2}}{n_g^2 \cos(\theta) + n\sqrt{n_g^2 - n^2 \sin(\theta)^2}} + \left| \frac{n_g^2 \cdot \cos(\theta) - n \cdot \sqrt{n_g^2 - n^2 \cdot \sin(\theta)^2}}{n_g^2 \cdot \cos(\theta) + n\sqrt{n_g^2 - n^2 \cdot \sin(\theta)^2}} \right|^2}{2} \qquad \text{Eq. (14)}$$

Note that the index of retraction $n_g$ will be relatively independent of temperature as long as the dipole moments of the individual molecules in the gas remain constant. For instance, monoatomic molecules such as in gaseous Argon could be expected to have relatively stable dipole moments over temperature. More complicated molecules such as H2O might be expected to have vibrational modes that would affect the dipole moment with increasing temperature.

FIG. 1 schematically depicts a sensor 10 that monitors gas density changes by monitoring changes in the index of refraction of the gas. A pressure vessel 11 includes two glass optical ports 12, 14 and a prism 16. The pressure vessel defines a vessel interior 18 that contains a pressurized gas mixture of 95% Ar and 5% He.

The prism 16 is composed of crown glass with an index of refraction of 1.523. The prism angles are as shown in FIG. 1. The prism angles are chosen to produce controlled optical paths for light entering the prism when the gas density inside the vessel 10 is that found at 20° C. and 3,100 psi. A principle ray 26 passing through the port 12 enters the prism 16 at an angle normal to a prism base 28 and strikes a surface 30 at the critical angle of 43.7°, as determined by equation 12 (with assumptions concerning the gas mixture and gas density at 20° C. and 3,100 psi) and is totally reflected. A reflected principle ray 32 passes through the prism 16 and strikes a prism surface 34 at the critical angel (approximately 43.7°) and is again totally reflected along a path 36. The reflected principle ray 36 then exits the prism through the base 28 and leaves the vessel 11 by the exit port 14.

A light ray 42, 44, 46 strikes the prism surface 30 at an angle less than the critical angle and is partially reflected at the surface 30 according to equation 14 and will be totally reflected at the surface 34.

A light ray 52, 54, 56 that strikes the prism surface 30 at an angle greater than the critical angle will be totally reflected at the prism surface 30 and will be partially reflected at the surface 34.

As the gas density rises above the 20° C., 3100 psi density the index of refraction $n_g$ of gas within the vessel interior 18 will increase as will the critical angle (via equation 12) and all light rays entering the prism 16 through the base 28 will be partially reflected at one or both of the prism surfaces 30, 34. When the gas density falls below the 20° C., 3100 psi density, the index of refraction and critical angle will decrease resulting in the principle ray 26, 32, 36 being totally reflected, at both prism surfaces 30, 34. For rays that are partially reflected, the power fraction of light reflected will be given by equation 14. As the gas density continues to fall, rays with angles close to those of rays 26, 32 and 36 will progressively begin to go into complete internal reflection at both faces of the prism. As a result, the amount of light making reflections will increase with decreasing gas density.

Figure 2:
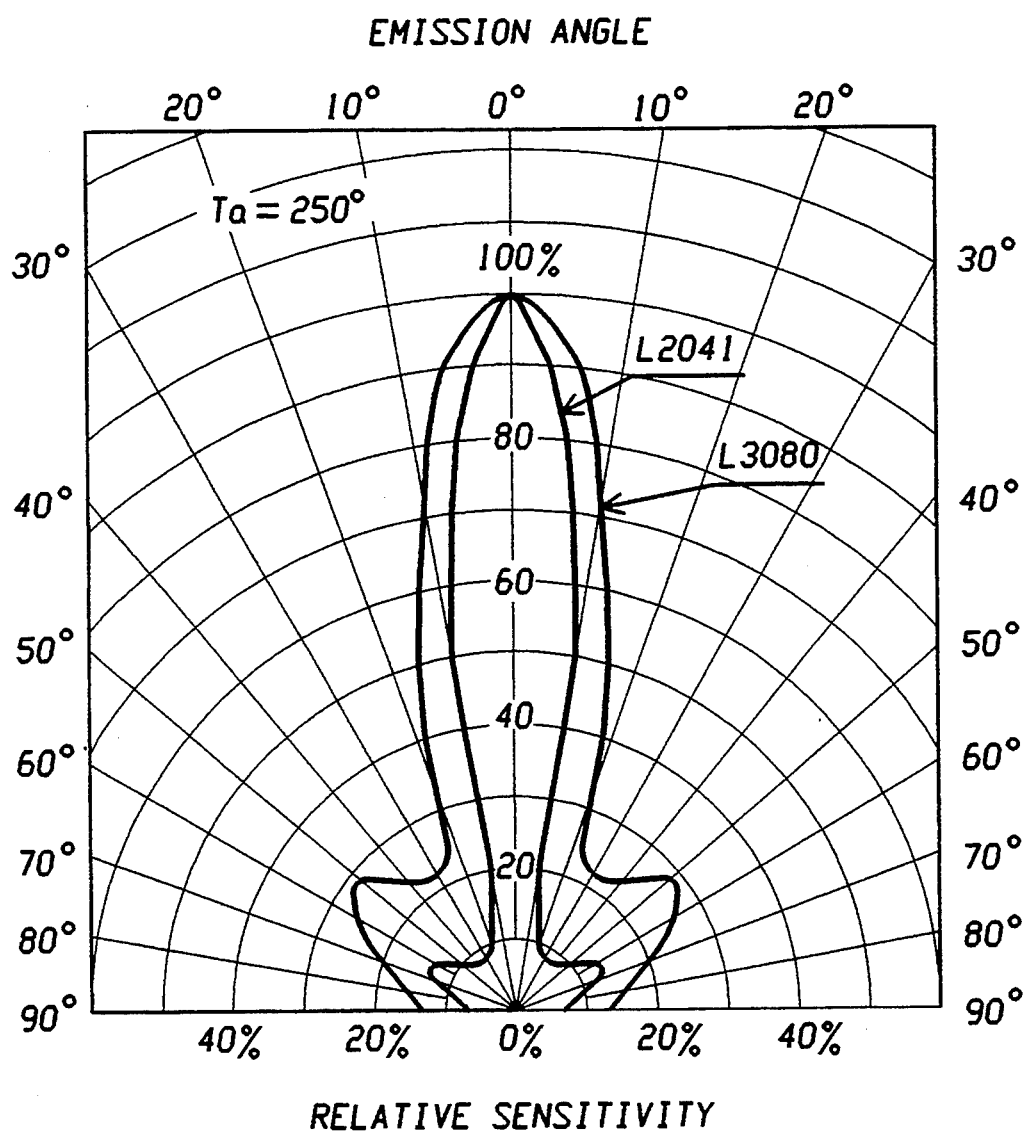
FIG. 2 is a graph showing light emitting diode output intensity as a function of angle.

In the preferred embodiment of the present invention, an infrared LED 60, (Hamamatsu part L3080) is placed in front of the port 12 to shine light through the port and into the prism 16. An infrared photodiode 62, (Hamamatsu part S2506) is placed in front of the port 14 as shown and a second 'reference' infrared photodiode 64, (Hamamatsu part S2506) is placed near the first LED 60 as shown. The LED 60 has an intensity vs. emission angle relationship such as is shown in FIG. 2.

The dimensions and separation of the ports 12, 14 limit the emission pattern that reaches the prism surfaces 30, 34 and passes through the exit port 14. Ideally, the emission pattern for the selected LED 60 would be sharply peaked at the center line to a region offset by 5 degree on either side of the centerline. However, in practice such tight emission patterns involve higher LED costs and require tighter assemble tolerance. By using a comparatively broad emission pattern such as shown in FIG. 2, the prism 16 remains well illuminated even if the LED 60 is installed with 5° of angular misalignment. As shown by the equations described above, the fraction of light beam reflected through the prism 16 back to the detector 62 is a function of the dielectric density of the gas under test, which is in turn strongly dependent on the gas density. However, the absolute strength of the light beam and as a result, the total amount of light reaching the photo detector 62, will depend directly on the amount of light emitted from the LED 60.

Emissions from an LED can vary with time (often decreasing), temperature and the amount of current drive. For instance, over a temperature range of $-40°$ C. to +85° C., a LED's light emission can vary by 50%. Over time, a LED's light emission can decrease to 80% or less of its initial level. Also, to a large extent, an LED's light emission will vary proportionally with drive current.

In contrast, the light current from a photodiode will be comparatively stable over time and temperature at a constant level of illumination. Additionally, light current from a photodiode will vary linearly with respect to the amount of illumination it receives over a broad range of illumination levels (assuming the illumination is in the photodiode's spectral range of sensitivity and does not vary in its spectral distribution). This comparative stability of photodiodes relative to LEDs is exploited by the use of the reference photodiode 64.

The reference photodiode 64 is placed so it is illuminated by light coming directly from the LED 60 along a light path 66. Light passing through the port 12 to the prism 16 and out the port 14 that reaches photodiode 62 will depend on the gas density (via equations 1–14) and on the amount of light emitted from the LED 60. Light reaching the photodiode 64 will depend only on the amount of light emitted from the LED 60. As a result, the ratio of the light currents from the photodiodes 62, 64 cancels out dependence on the amount of LED emission and varies primarily with gas density, i.e., if the LED 60 light emission increases by 30%, the light currents from the photodiodes 62, 64 will both increase by 30%.

Figure 3:
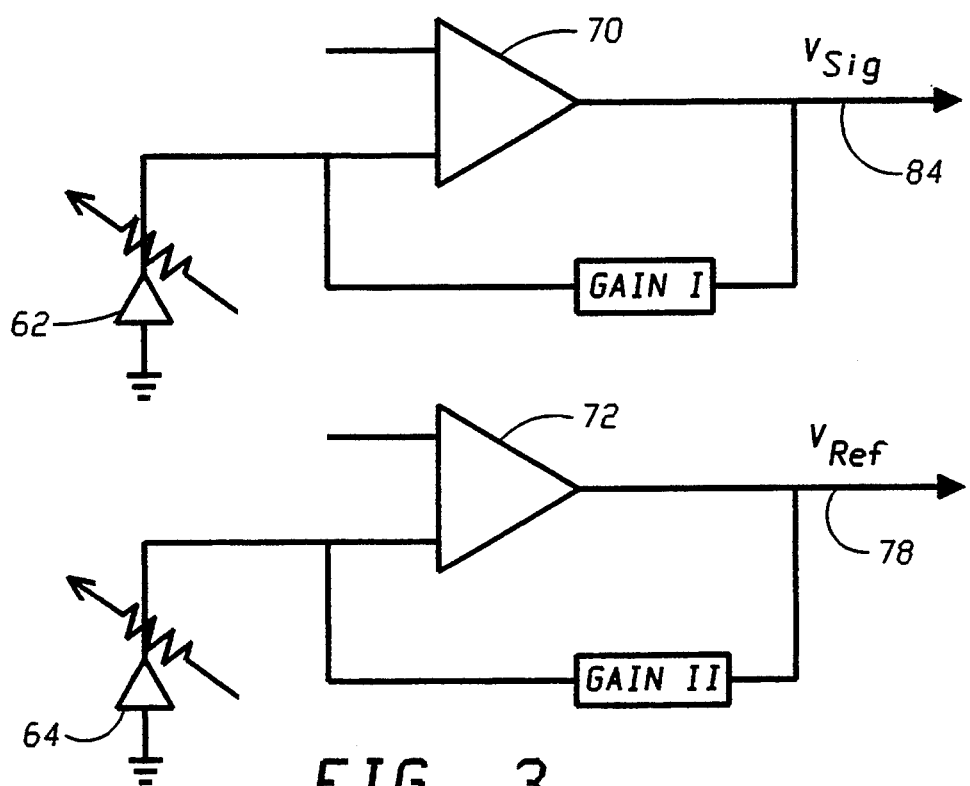
FIGS. 3 and 4 are schematic depictions of circuits for energizing a light emitting diode and monitoring signal outputs from two photodiodes.

In the preferred embodiment, the light current from each photodiode 62, 64 is amplified to produce a voltage that varies directly with light current and amplifier gain as shown in the simplified schematic in FIG. 3. When the sensor 10 is assembled, the gains of two amplifiers 70, 72 are adjusted to produce a preselected voltage 'Vref' from the reference photodiode and a preselected voltage 'Vsig' from the signal photodiode at a preselected calibration gas density 'Dcal' at a calibration temperature 'Tcal'.

Figure 4:
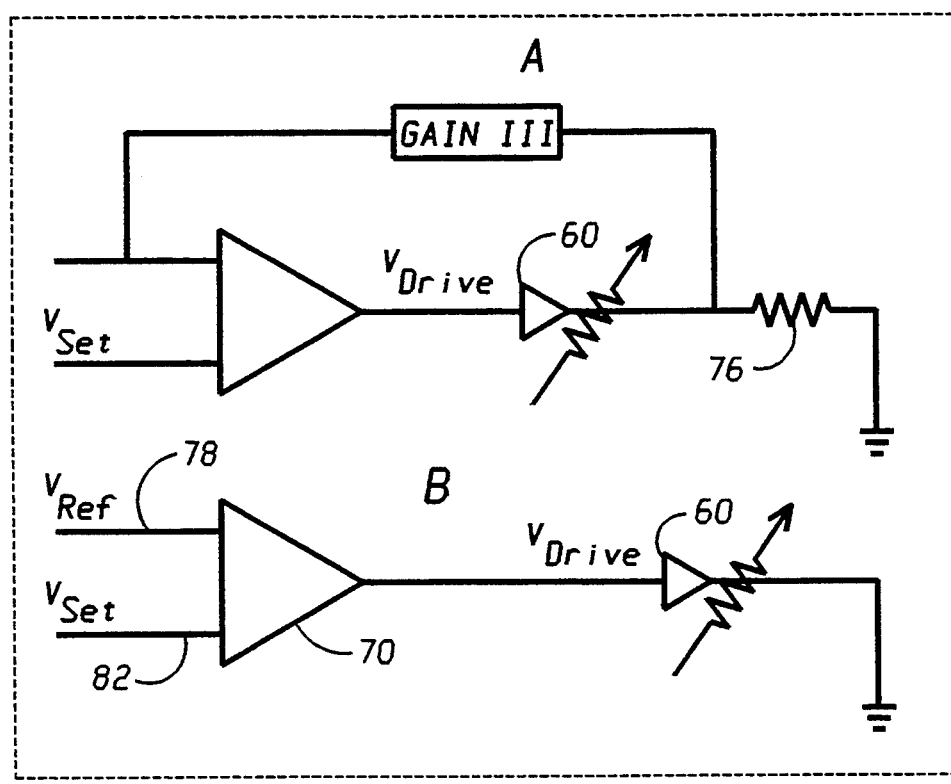

The LED 60 is driven in one of two ways (see FIG. 4). In method A, the voltage across a resistor 76 in series with the LED 60 is kept constant. This results in a constant current drive mode for the LED 60. In method B, a Vref signal 78 from the reference photodiode 64 is fed back into an LED drive amplifier 80 which in turn alters Vdrive to keep Vref equal to a control voltage Vset 82. This effectively keeps the light output from the LED 60 constant despite variations in its emission or emission efficiency with respect to changes due to an otherwise variable drive level, temperature or aging. Method B is the preferred mode if the output Vsig 84 is going to be used as an analog indication of gas density. Method A is useful when all that is required is a 'greater than' comparison between Vsig 84 and Vref 78 for switchpoint gas density detection. It is also useful in situations where overall current usage must be controlled.

Figure 5:
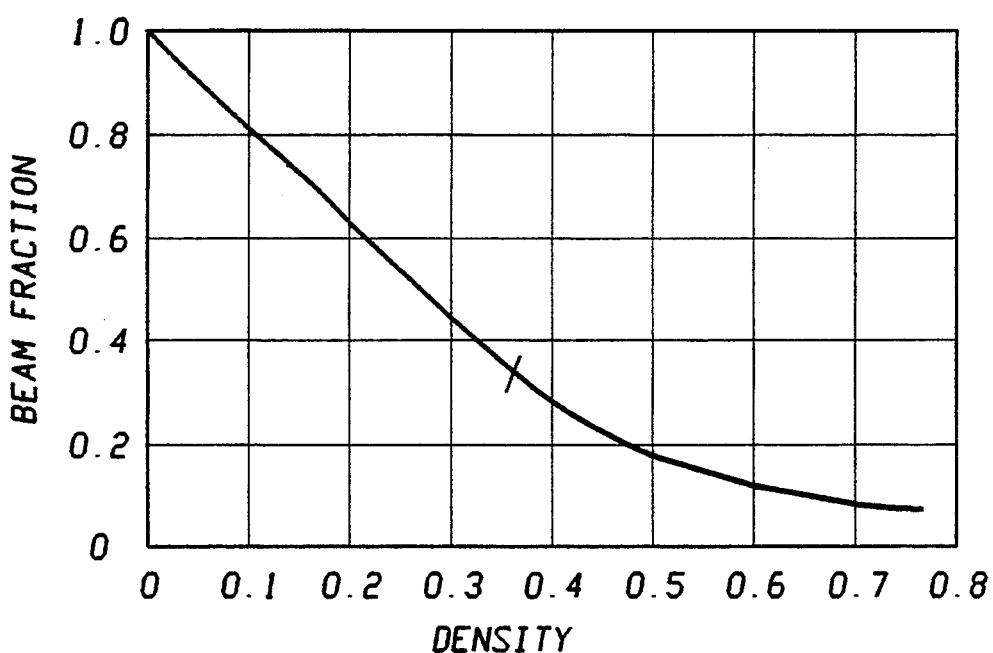
FIG. 5 is a graph showing theoretical sensed light intensity as a function of gas density based upon derived equations.

Given an angular acceptance of about 5° and the arrangement of FIG. 1, the fraction of the LED beam that can be expected to reach the photo detector 62 is shown as a function of gas density in FIG. 5 (curve is for pure Argon). Note the curve is normalized relative to the fraction predicted at a density of 0.0017832 g/cm$^3$ (20° C. and 760 mmHg density). As can be seen, there is an approximately linear relationship between the beam fraction and density up to the critical density of 0.35 g/cm3. Thereafter the beam fraction shows a slow exponential decrease.

The linear region, 0.0018932 to 0.35 g/cm$^3$, corresponds to the density range where some fraction of the central ±5° of LED beam is totally reflected at prism surfaces 30, 34. As shown in equations 1–12 for a small electric susceptibility X, the relationship between critical angle and gas density is approximately linear. The portion of the ±5° beam emission that is totally reflected through the prism can then be expected to be approximately linear in gas density. Since the totally reflected beam component will have a much higher energy than the partially reflected component (see equation 14), an approximately linear relationship between the total amount of light reflected through the prism 16 and gas density is seen. Above the 0.347 g/cm3 gas density, the only beam components that make it through the prism are those that are partially reflected from prism surfaces 30, 34. Referring to equations 10, 12 and 15, one sees that little linearity in partial reflections vs. density are expected.

Figure 6:
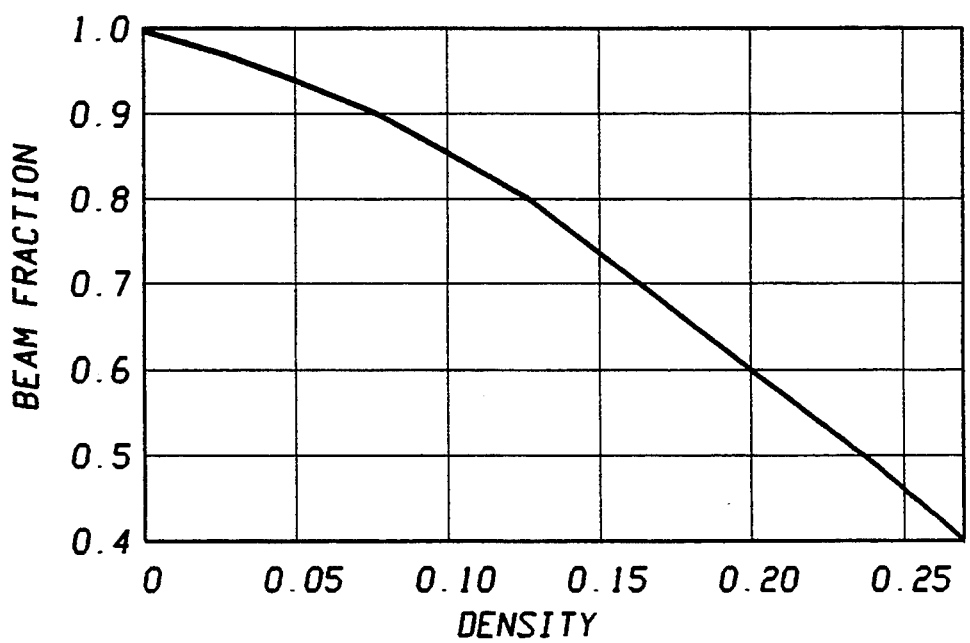
FIG. 6 is graph showing experimental test data confirming the theoretical plot of FIG. 5.

At a constant temperature the gas density would be expected to vary approximately linearly with pressure. In FIG. 6, normalized beam fraction reaching the photo detector 62 vs. gas density data is shown for pure Argon gas and a prism 16 and pressure vessel 11 constructed according to FIG. 1. As can be seen, the relationship is approximately linear up to the highest pressure. A strong and monotonically decreasing relationship between beam fraction and density is shown. This is in general agreement with the type of behavior anticipated by the preceding analysis. Note that in FIG. 5, the predicted beam fractions are approximately 0.8, 0.65 and 0.4 at gas densities of 0.12, 0.2 and 0.27 respectively. In FIG. 6, experimental data show that the actual beam fractions at the same densities are 0.81, 0.6 and 0.4 respectively. This shows a good agreement between theory and practice for the sensor 10.

A major advantage of the invention is the fact that the light signal follows the unchanging path of the optics without physically contacting the gas under test. As long as the prism surface is "wetted" by the gas within the vessel 11, the light signal should be relatively immune to dust contamination or variations in gas color and light absorption characteristics. Additionally, the reflection effect in the prism is affected by the gas density, not the gas temperature or pressure. As a result, the sensing effect is highly stable against changes in temperature and pressure at the same gas density. On the other hand, knowledge of temperature and gas law for a given gas allows the density measurement to also be used in determining pressure.

Figure 7:
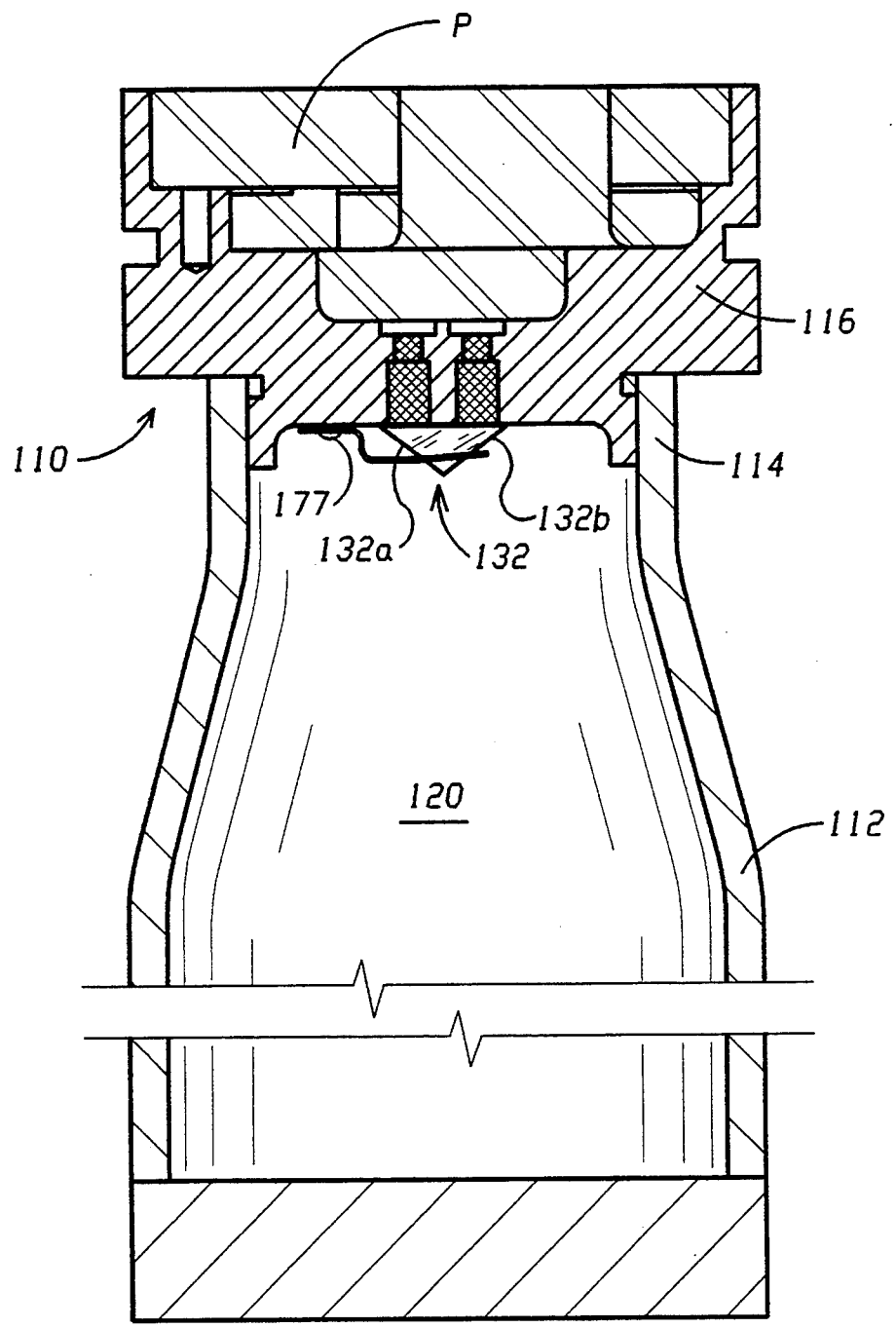
FIG. 7 is a section view of a sensor connected to a vessel containing a fluid whose density is determined.
Figure 7A:
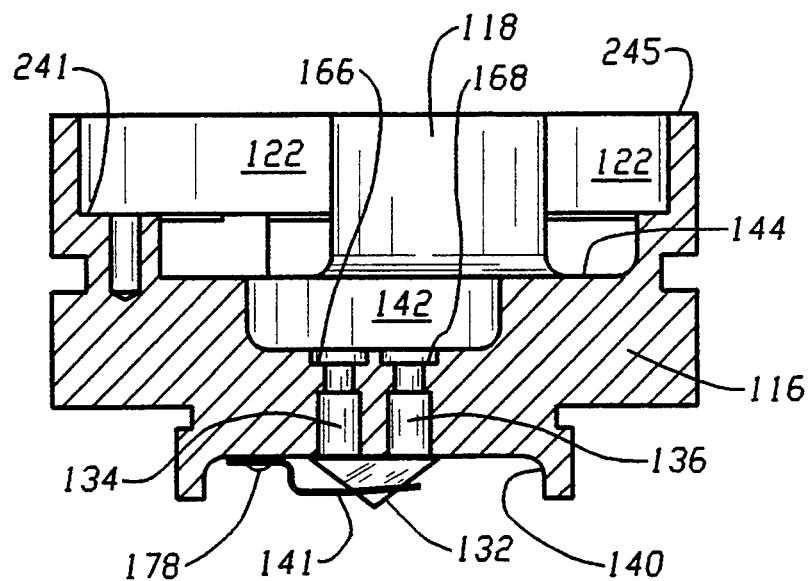
FIG. 7A is a section view of a sensor body for supporting a gas density sensor constructed in accordance with the present invention.
Figure 8:
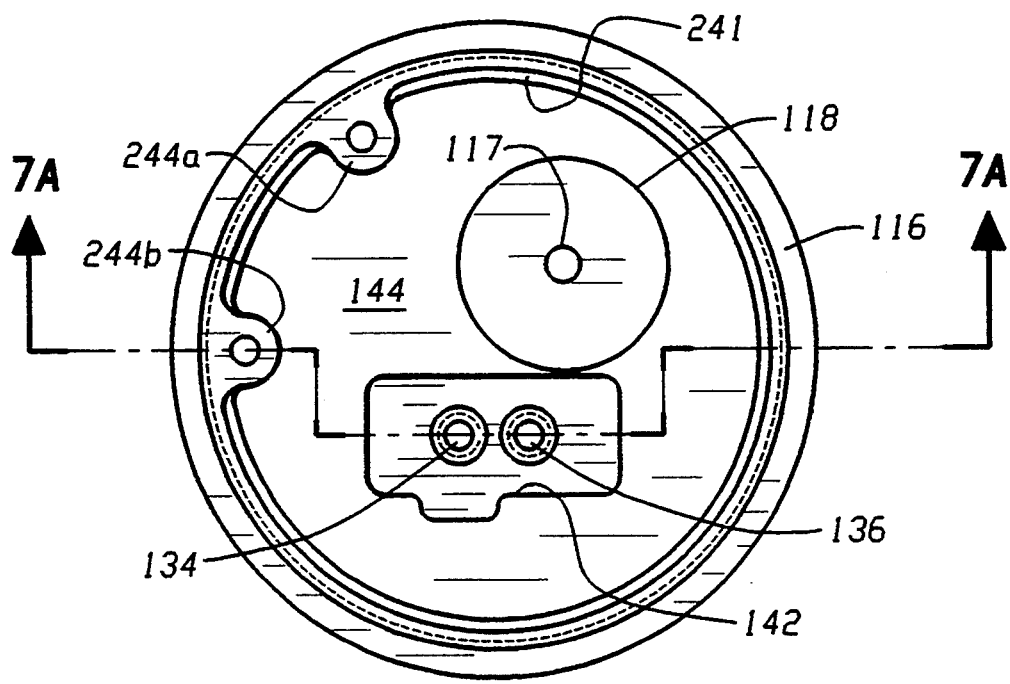
FIG. 8 is a plan view of the FIG. 7A sensor body.

FIGS. 7, 7A and 8 depict a sensor 110 constructed in accordance with a preferred embodiment of the present invention. The sensor 110 is coupled to a vessel 112 having a necked down end 114 that engages the sensor 110. A sensor body 116 defines a fill hole 117 which extends through a cylindrical post 118 of the body 116 and opens into an interior 120 of the vessel. The fill hole 117 allows fluid whose density is under determination to be injected into the vessel 112.

Figure 13:
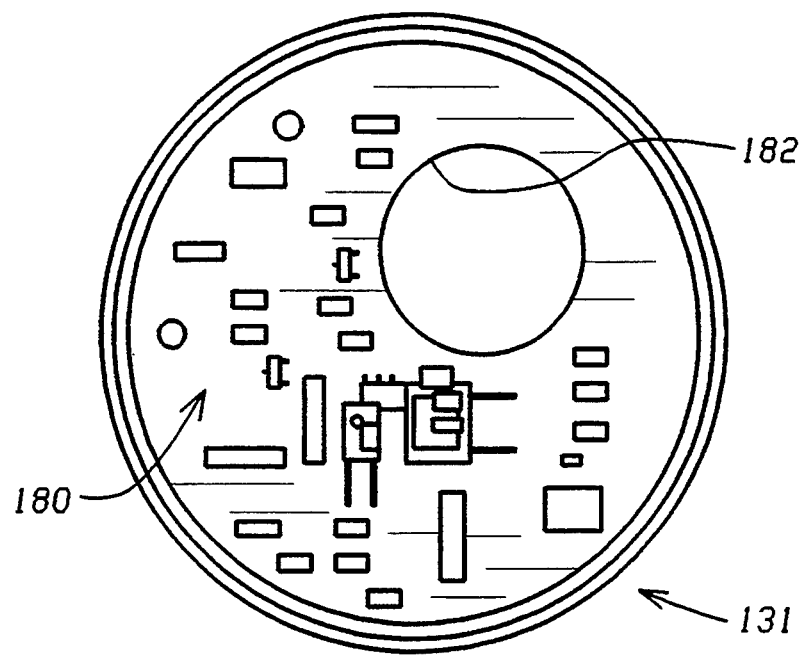
FIG. 13 is a plan view of a circuit board supporting electronics for activating the gas density sensor.

The sensor body 116 is formed from metal and includes a cavity 122 into which an optical subassembly 130 and printed circuit board 131 (FIG. 13) are inserted. During fabrication of the sensor 110, a prism 132 is fixed to the sensor body 116 in a position that covers two glass-filled optical ports 134, 136 in the sensor body 116. The optical ports 134, 136 transmit light from a light-emitting diode 60 mounted to the optical subassembly 130 into the prism. The prism has surfaces 132a, 132b in direct physical contact with a gas within the vessel interior 120.

A cavity or recess 140 is machined in the sensor body 120 so that after the prism 132 is attached to the sensor body the prism is protected from damage. During shipment of the sensor 110, a removable protective boot (not shown) also covers the prism 116. A metal clip 141 (FIGS. 14, 15) is also attached to the sensor body 120 to prevent movement of the prism 132 if the attachment between the prism 132 and sensor body 116 should loosen.

Figure 9:
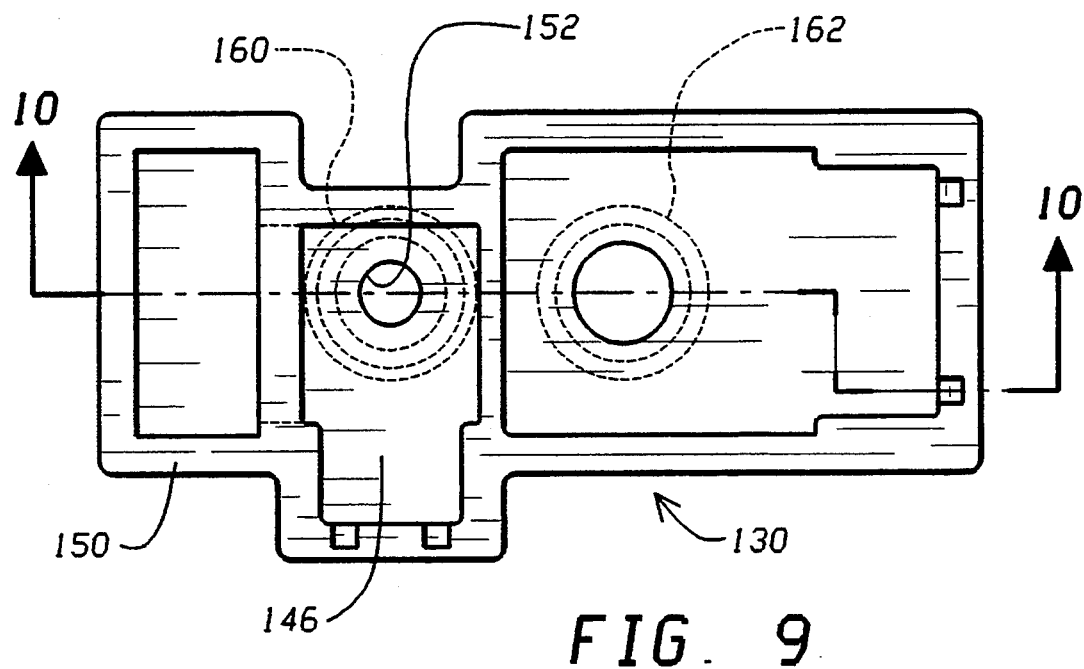
FIG. 9 is a plan view of an optical subassembly of the FIG. 7 sensor.
Figure 10:
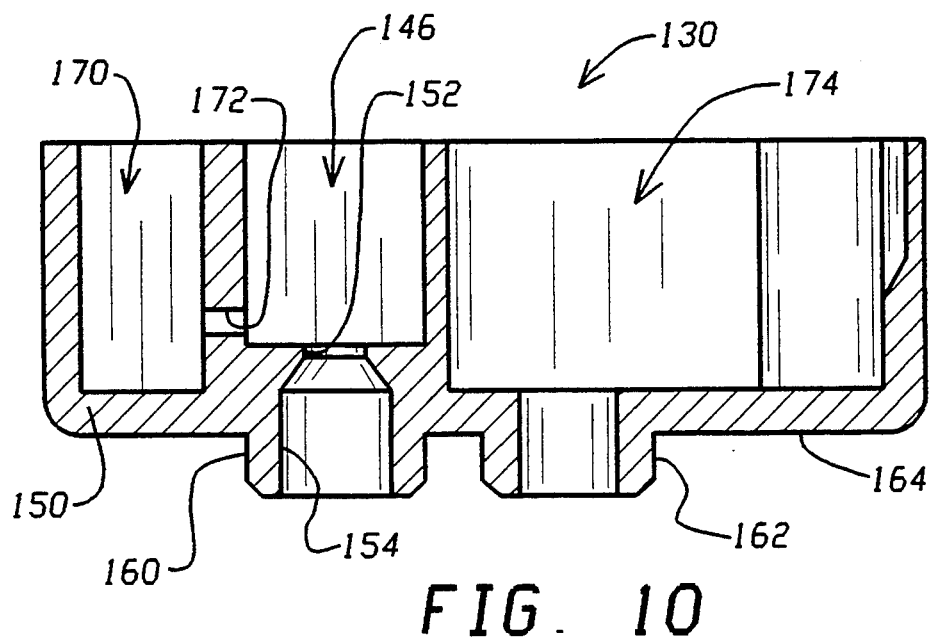
FIG. 10 is a view as seen from the plane 10—10 in FIG. 9.

The optical subassembly 130 is depicted in greater detail in FIGS. 9 and 10 of the drawings. A well 142 in the sensor body extends beneath a base 144 of the cavity 122. The well 142 is shaped to receive the optical subassembly 130 as the sensor is being built. When inserted into the well, the subassembly 130 positions the LED 60 in a region 146 so that light emitted from the LED 60 passes through the optical port 134 and into the prism. When mounted to the subassembly 130 the LED 60 abuts an exit aperture 152 (FIG. 10) that opens into a passageway 154 leading to the optical port 134.

A carrier member 150 defines two annular bosses 160, 162 that extend outwardly from a bottom surface 164 of the carrier 150. These bosses 160, 162 seat within counterbores 166, 168 in the sensor body and help position the carrier 150 as the sensor 110 is assembled.

The optical subassembly 130 also supports two photodiodes 62, 64 for monitoring light emissions from the light-emitting diode 60. A reference photodiode 64 is positioned within a cavity 170 so that a small percentage of the light generated by the light-emitting diode 60 passing through a passageway 172 reaches the photodiode 64. The second photodiode 62 is positioned in a cavity 174 to monitor light passing through the optical port 136 that has been twice reflected at the two surfaces 132a, 132b between the prism and gas within the vessel interior 120. By monitoring a ratio of the outputs of these two photodiodes 62, 64, a determination of the fluid density widen the vessel can be made.

Figure 14:
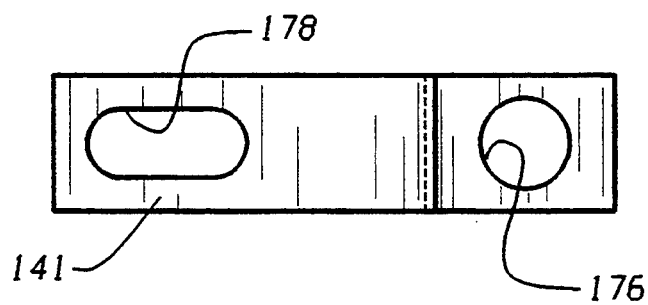
FIGS. 14 and 15 are plan and elevation views of a clip for holding a glass prism inside a pressure vessel.
Figure 15:
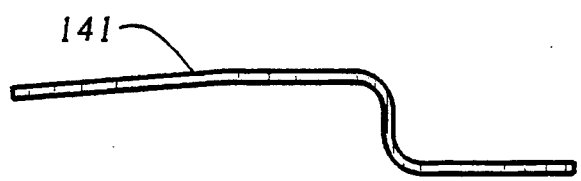

As seen :most clearly in FIGS. 14 and 15, the clip 141 is a stamped flat metal piece bent along its length and including a mounting opening 176 to allow a connector 177 (FIGS. 7, 7A) to connect the clip 141 to the sensor body. A second opening 178 overlies a prism apex and assures the prism will not separate from the sensor body.

Figure 20A:
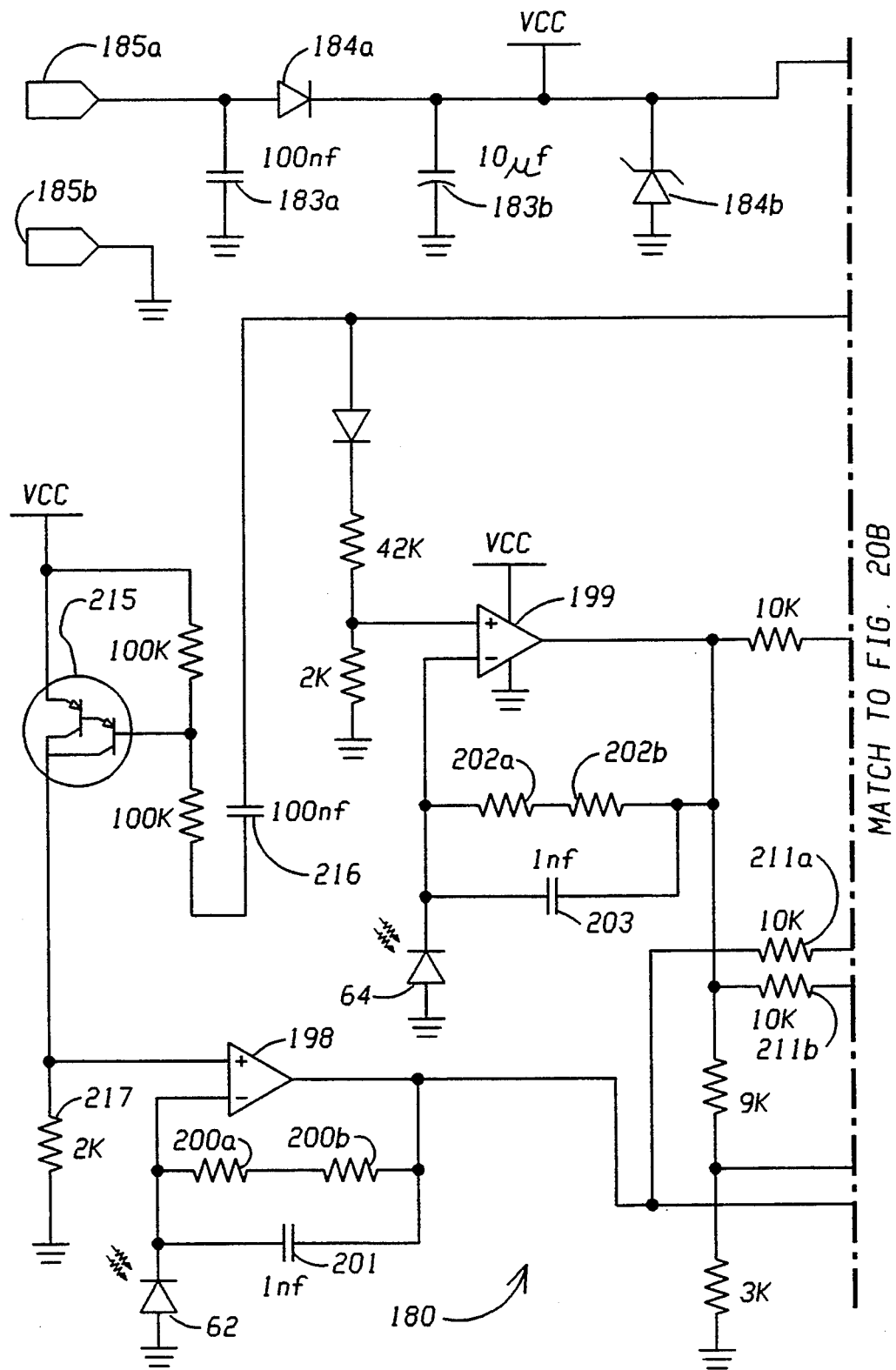
FIGS. 20A and 20B are more detailed schematic diagrams of circuitry for activating a light emitting diode.
Figure 20B:
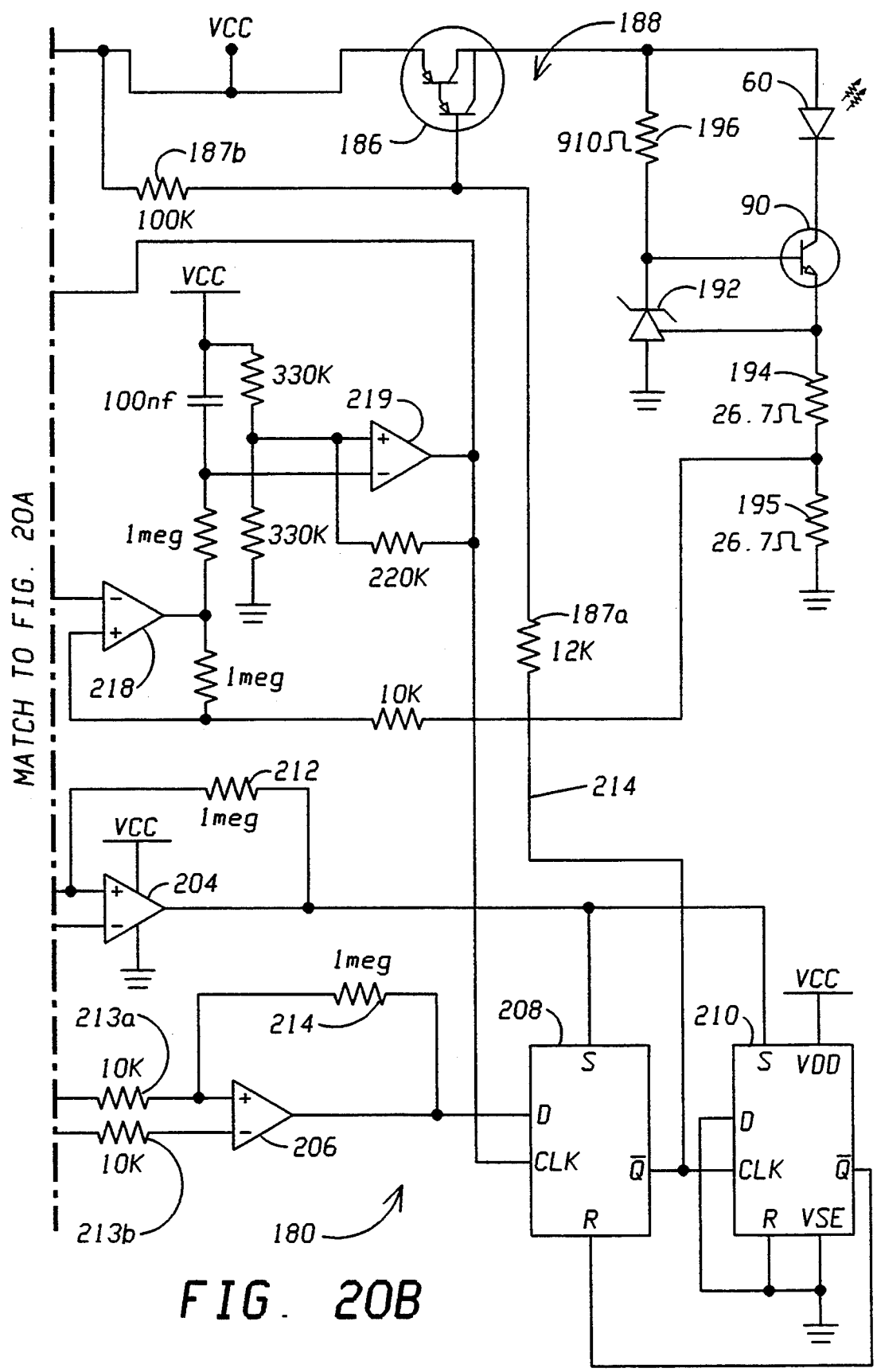

Circuitry 180 (FIGS. 20A, 20B) for activating the light-emitting diode 60 and monitoring output signals from the two photodiodes 62, 64 is supported on the printed circuit board 131. An opening 182 in the circuit board 131 fits over the column 118 in the sensor body 116 to allow the board to be placed into the recess 122 in the sensor body 116.

Two capacitors 183a, 183b and two diodes 184a, 184b provide input noise filtering and overvoltage protection to the circuit 180. The capacitor 183a provides a low impedance path across the input terminals 185a, 185b to shunt high frequency noise around the circuit 180 and protect against electrostatic damage. The diode 184a prevents reverse polarity current flow. The capacitor 183b acts as a DC noise filter and the diode 184b provides overvoltage protection by clamping the voltage across inputs 185a, 185b to the circuit to a maximum value.

A transistor 186 and biasing resistors 187a, 187b form a solid state switch 188 for providing power to the circuit 180. The resistor 187a limits current to the base of the transistor 186 and the resistor 187b provides pullup voltage to the base when the transistor 186 turns off.

The light-emitting diode 60 is coupled to the collector of a transistor 190. When the transistor 190 conducts, the diode 60 conducts and emits an infrared output. A precision regulator 192 (Texas Instrument's Part No. TL431IPK) maintains a constant current through two resistors 194, 195 by controlling the base current through the transistor 190. Current at the base of the transistor 190 creates collector-emitter current flow through the transistor 190 to develop a voltage drop across the resistors 194, 195. The voltage generated across the resistors is used by the precision regulator 192 to control base current of the transistor 190. The collector to emitter current through the transistor 190 is the same current that flows through the infrared emitting diode 60. A resistor 196 acts as a current limit and series voltage drop for the regulator 192.

Signals developed by the two photodiodes 62, 64, in response to an infrared light output from the light-emitting diode 60, are applied to two precision operational amplifiers 198, 199. Light striking the detector 62 generates current flow from the cathode to the anode of the detector. The output voltage developed by the operational amplifier 198 increases until the current through a pair of factory settable based upon circuit performance feedback resistors 200a, 200b is equal to the current through the diode 62. A capacitor 201 filters high-frequency noise from the gain loop of the operational amplifier 198.

In a similar fashion, the current through the diode 64 generates current flow from its cathode to anode. The voltage developed at an output from the operational amplifier 199 increases until the current through the series feedback resistors 202a, 202b equals the current through the diode 64. A capacitor 203 filter high-frequency noise from the gain of the operational amplifier 199.

The output from the operational amplifier 199 is a signal related to the strength of the output from the light-emitting diode 60 without the affect of gas density. This output is coupled to two comparator amplifiers 204, 206 (FIG. 20B), having outputs coupled to two latch circuits 208, 210. An output from the operational amplifier 198 is also coupled to the comparator amplifier 204. The comparator 204 compares the voltage signal output from the reference photodiode 64 with the signal output from the receiver photodiode 62. Two resistors 211a, 211b at the inputs to the comparator 204 prevent overloading of those inputs. A feedback resistor 212 provides positive feedback and prevents oscillation of the output from the comparator amplifier 204.

In a similar fashion, two input resistors 213a, 213b prevent overloading of the comparator 206. A feedback resistor 214 produces a positive feedback and prevents oscillation of the output from the comparator 206.

The latch circuits 208, 210 control application of power to the light-emitting diode 60. When the inverted output 214 (not Q) from the latch 208 allows the base of the transistor 186 to go high, the light-emitting diode 60 is extinguished. When this occurs, the latch 210 receives a clock input and prevents the latch 208 from again turning on the light-emitting diode 60. If the signal from the comparator 198 is less than or equal to the signal from the comparator 199, the output from the comparator 204 will be high.

A power-ON reset function is supplied by a transistor 215 and a charging circuit that includes a capacitor 216.

The transistor 215 turns on when power (VCC) is applied to the circuit 180. As the transistor 215 conducts in response to the power input, a voltage drop develops across a resistor 217 coupled to the non-inverting (+) input to the operational amplifier 198. This positive saturation of the operational amplifier 198 causes the comparator 204 to output a positive or high-level signal which sets the outputs of the two latch circuits 208, 210. When the latch 208 is set, its inverted output (not Q) goes low, causing the transistor 186 to conduct causing the light-emitting diode 60 to produce an output signal.

After a 15-millisecond delay, the capacitor 216 has charged to the point that the transistor 215 is rendered non-conductive. This allows the operational amplifier 198 to produce a valid signal from the photo detector 62. Stated another way, for the first 15 milliseconds that power is applied to the circuit 180, no valid signal is generated.

An operational amplifier 218 has a reference input (+) coupled to a resistance divider formed by the resistors 194, 195. This operational amplifier 218 inhibits operation of the delay circuit signal output from the operational amplifier 219. If the signal at the junction between the two resistors 194, 195 falls below a certain level, voltage applied to the circuit is too weak for continued operation and the latch delay circuit is inhibited.

When power is applied to the circuit at the input 185a, an output from a comparator 219 goes low. At the same time, the transistor 215 turns on, making the output of the operational amplifier 198 go high. This high output is coupled to the operational amplifier 204 and causes the output from this operational amplifier to set the latch circuits 208, 210. This turns on the transistor 186 and supplies power to the light-emitting diode 60. As the capacitor 216 charges, the transistor 215 turns off, allowing the operational amplifier 198 to monitor signals derived from the photodiode 62.

An output from the operational amplifier 218 stays low as long as the signal strength from the reference photodiode operational amplifier remains higher than the voltage from the reference input voltage supplied by the voltage divider formed by the resistors 194, 195 of the light-emitting circuit. The output from the comparator 218 goes high, however, if the reference voltage from the resistors 194, 195 is not high enough. When the output from the comparator 218 goes high, it inhibits the output from the comparator 219. If the reference signal at the junction of the resistors 194, 195 is high enough, the output from the comparator 219 goes low at applied power and switches to high approximately 100 milliseconds after power is applied to the circuit. The transition of the output from the comparator 219 from low to high that latches the "good or bad" reading of the sensor once power is applied. If the output from the comparator 198 that is applied to the comparator 204 is higher than the reference input to the comparator 204, the comparator 204 outputs a high signal which overrides the inputs to the latches and keeps their outputs in their set state. This output goes high if the output from the signal receiver is low, indicating a fault in the circuit 180.

The circuit 180 is tied to a monitoring circuit (not shown) which determines the density of the gas by monitoring current passing through the transistor 186 and LED 60. If the sensed density is below a threshold value, the light-emitting diode 60 will remain on and the monitoring circuit will sense a current draw of approximately 50 mA by the circuit 180. So long as the gas density stays above a specified level, indicating a certain amount of gas remains within the vessel, a 5-milliamp (approximately) quiescent current is drawn by the circuit 180.

The preferred use of the sensor is in an automobile where a Helium-Argon gas within an air bag system is checked each time the automobile is started. The external monitoring circuit checks the gas density and, if too low a density is sensed, the motorist is warned that the air bag system needs maintenance.

Figure 11:
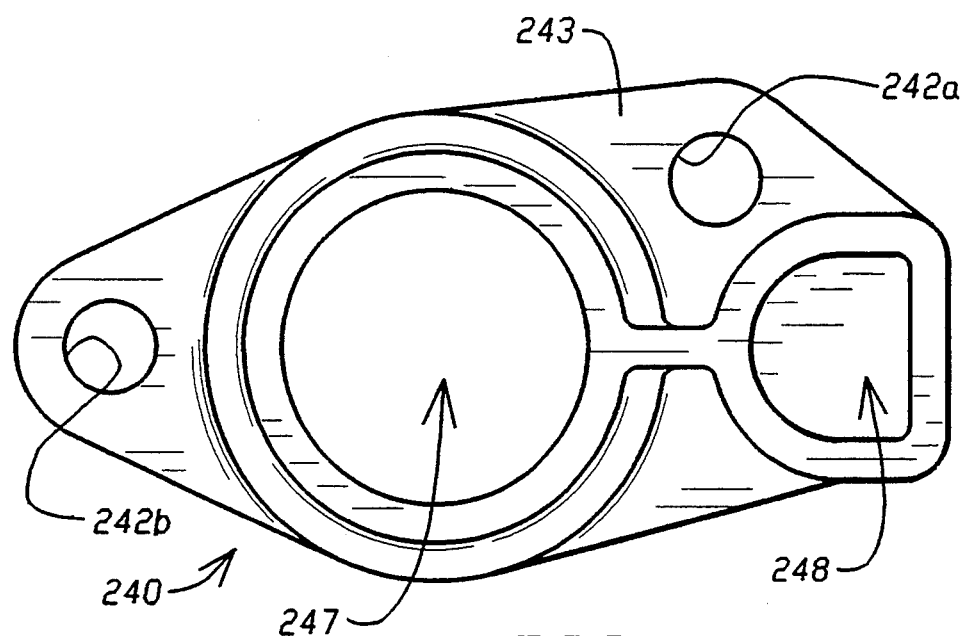
FIG. 11 is a plan view of a connector for routing electric signals into the sensor body of FIG. 7A.
Figure 12:
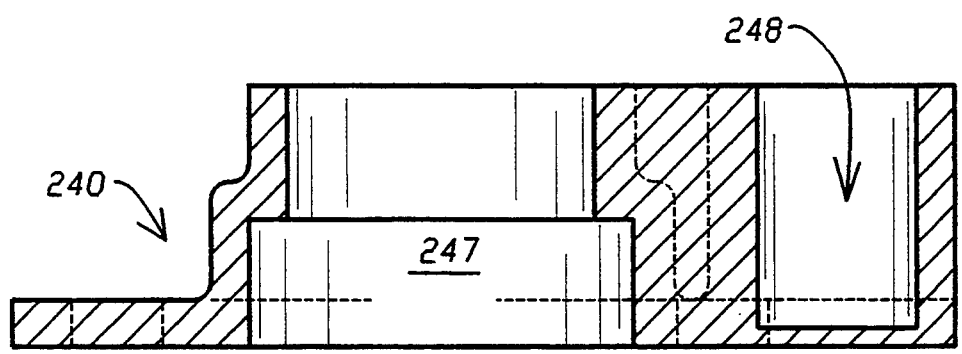
FIG. 12 is a section view of the FIG. 11 connector.

The first two circuit inputs 185a, 185b to the circuit 180 are located outside the sensor body 116. Leads enter the body through a plastic connector 240 (FIGS. 11 and 12). The circuit board 131 is placed into the cavity 122 and rests against a recessed ring 241 of the body 116 (FIG. 8). The connector 240 is placed into the cavity 122 so that two openings 242a, 242b of a connector flange 243 align with two tabs 244a, 244b in the ring 241. When seated against the tabs, the connector 240 extends slightly above an upper rim 245 of the body 116.

Once the connector 240 has been attached to the body with suitable connectors, a region between the connector 240 and an inner wall 246 is filled with a potting compound P. A throughpassage 247 in the connector leaves regions of the circuit exposed for attachment of leads to the circuit board 130. These leads are carried by a harness (not shown) connected to a source of an input voltage. The harness includes a tab that fits into an opening 248 in the connector that prevents rotation of the wiring harness connector.

Alternate Embodiment No. 1

Figure 16:
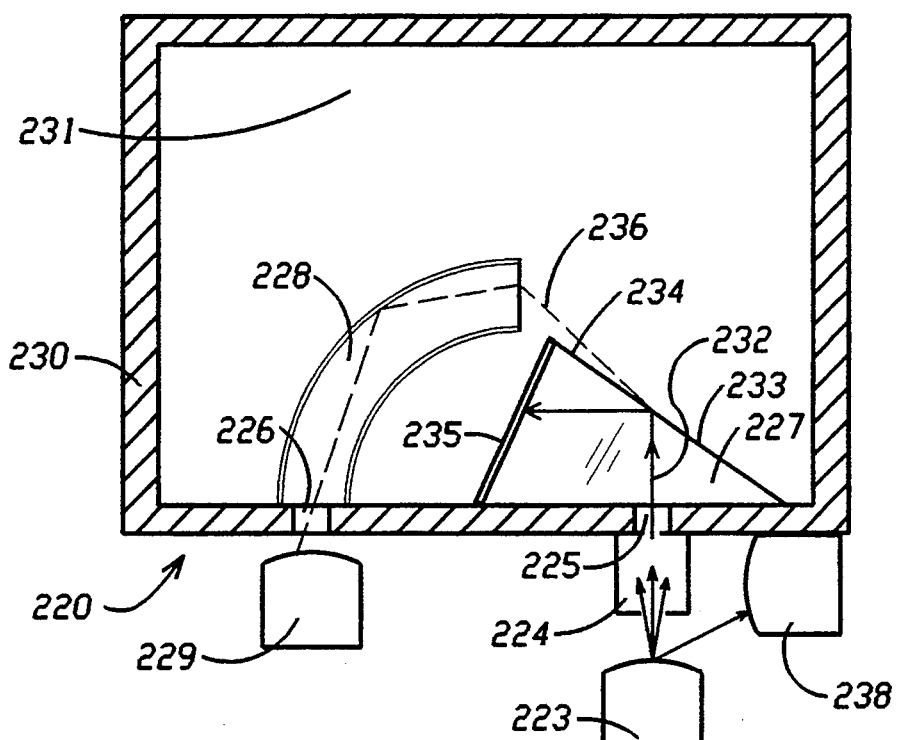
FIG. 16 is a schematic representation of an alternate fluid density sensor.

An alternate embodiment of the invention is shown in FIG. 16 where a sensor assembly 220 includes a light source 223 (laser, laser diode, lamp or LED), a collimating element 224 (lens and/or aperture stop assembly), two optical ports 225, 226, a prism 227, a light collector 228, a photodetector 229 (photodiode, phototransistor, photocell etc.), and a pressure vessel 230 having an interior 231 filled with a gas, is shown in FIG. 16. The collimating element 224 and source 223 are aligned so that the right edge of the beam 232 strikes a prism face 233 at the critical angle for a reference gas density (nominally the gas density observed at 760 mm and 20° C.).

When the gas inside the vessel 230 is at or below the reference density, all of the beam 232 will be totally reflected at the prism face 233 and will strike a prism face 234 and be absorbed by a black coating 235. When the gas inside the vessel 230 rises in density above the reference gas density, the right most portion of the beam 232 will begin to be partially refracted. A refracted portion 236 of the beam will then strike the light collector 228 and be directed through the port 226 to the detector 229.

As the gas density rises, more and more of the beam will be partially refracted and be directed to detector 229. This will result in a monotonically increasing signal with increasing density.

The functional relationship between the signal from the detector and gas density are optimized towards a desired behavior by selection of beam width and reference gas density. Advantages include a signal that increases with increasing gas density as opposed to decreasing with increasing gas density (as in the preferred embodiment). As in the preferred embodiment, instability in the light source 223 can be canceled out with the use of a reference detector 238. The choices of electronics will be driven by the type of light source and photodetectors that are selected. However, in general, an amplifier would be provided for each photodetector 229, 238. The light source could be driven in constant current or constant light emission mode in a fashion analogous to that described for the preferred embodiment and shown in FIGS. 3 and 4.

Although not explicitly shown in FIG. 16, a useful deployment for this alternate embodiment is to separate the portion of the pressure vessel containing the ports, prism and electro-optics. This portion is then provided as a threaded or weldable insert that can be installed in any suitably ported pressure vessel.

Further Embodiments and Applications

Nominally, glass and plastic optics will have indices of refraction on the order of 1.5 or greater. Pressurized gasses such as Argon in the 14.22 to 4600 psi range at 20° C., can be expected to have indexes of refraction that are in the 1.000 to 1.1 range. A liquid such as water or chemical mixtures with water as a solvent, can be expected to have indices of refraction on the order of 1.33. Other liquids such as Cineole, Aniline and benzine have indices of refraction of 1.456, 1.584 and 1.498 respectively.

The devices described in the preceding embodiments would have ready application to measuring the density of other gasses besides Argon and Helium. They could also be used to determine the relative concentrations of two gasses of different molecular dipole moments at a given pressure and temperature. In this technique a gas of higher dielectric constant is mixed with one of lower. The overall index of refraction would then vary with the relative concentrations of the mixed gasses.

Given a liquid solvent of known index of refraction such as Water, Cineole, Benzine or even Oil, the disclosed technique could be used to measure the relative abundance of any chemical dissolved in or mixed with the solvent, provided the chemical that was added effected the index of refraction. Devices based on the preferred embodiment would not even require transparency in the tested solution as the device is sensitive to index of refraction of the tested medium and not its transparency. Applications could include measuring the antifreeze concentration in a radiator, gasoline contamination in engine oil, battery and concentration and contaminants in other chemicals.

Figure 17A:
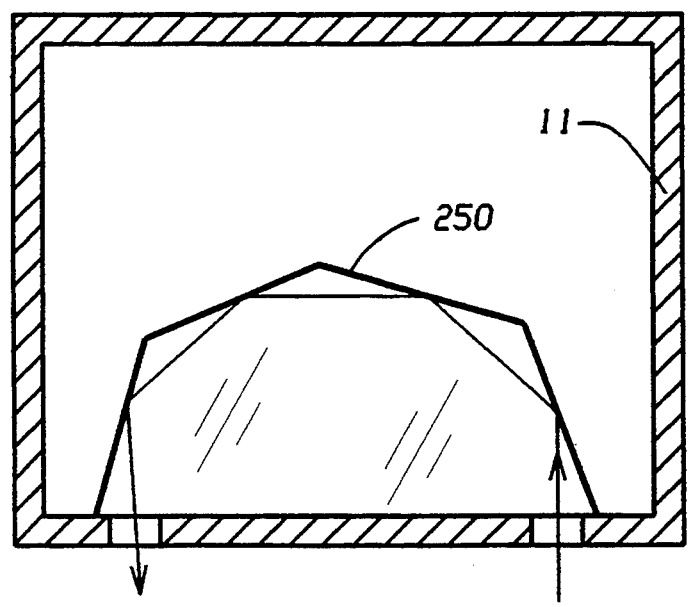
FIGS. 17A–17C are schematics of multiple alternate ways of prism mounting configurations.
Figure 17B:
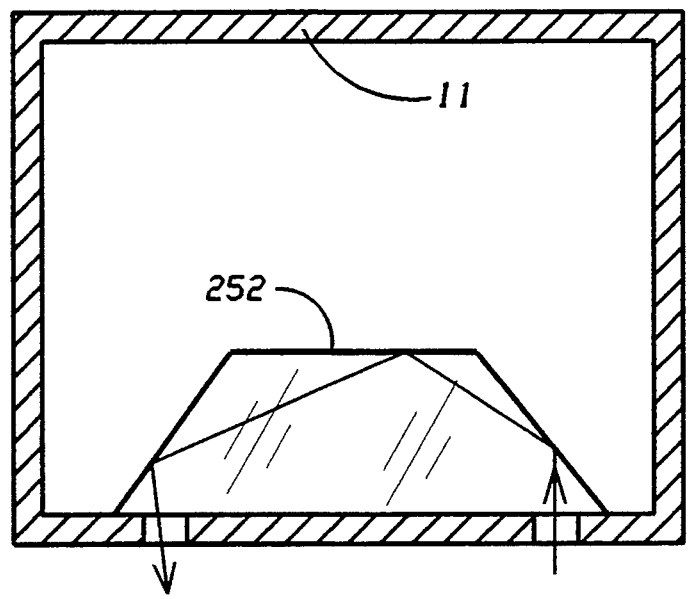

In instances where the angle of total reflection is large, multifaceted prisms 250, 252, such as those shown in FIGS. 17A, 17B, would be used. In cases where the index of refraction in a liquid is sensitive to temperature, pressure, aging or some other parameter, the embodiments described could be used to measure that parameter as well.

Embodiment for High Index of Refraction Media

Figure 17C:
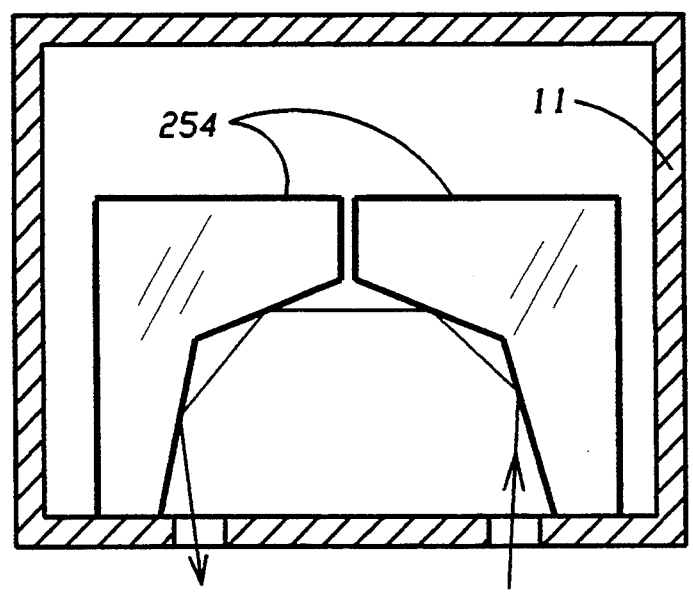

For substances with an index of refraction greater than that of the optics material an arrangement such as is shown in FIG. 17C could be used. Here, a prism 254 has facets on the *inside of an otherwise solid block of dielectric material. The medium trapped within the prism cavity would then function as the prism. A disadvantage of this method would be that the signal (reflected) light would have to pass through the tested medium and would be susceptible to changes in transparency as well as index of refraction.

Single Light Path Embodiment

Figure 19:
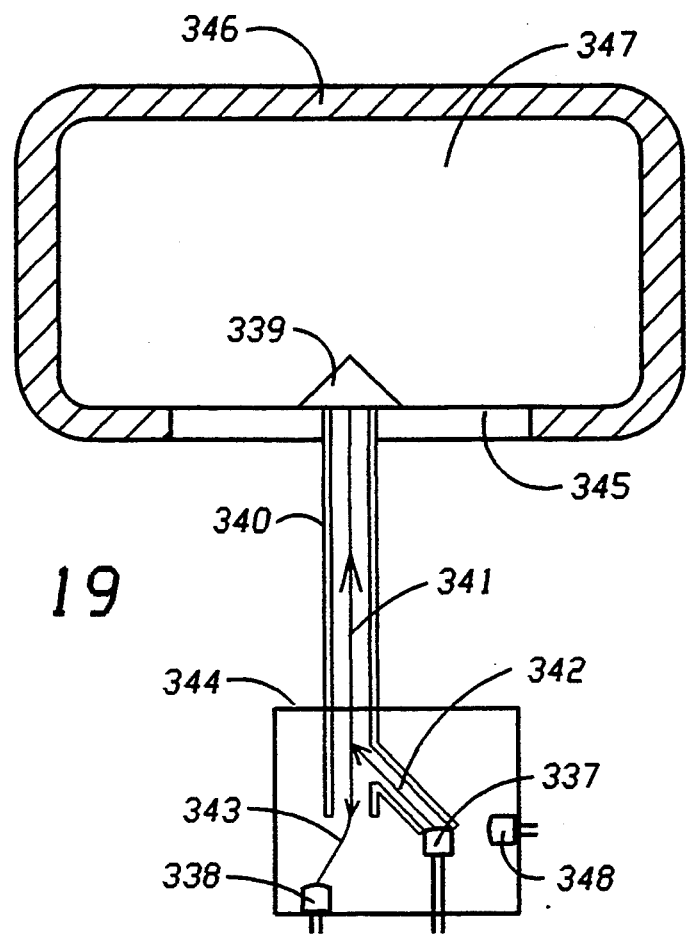
FIG. 19 is an alternate embodiment of the invention that uses a single entrance and exit light path.

In all the previous embodiments, two optical ports are shown. This is not a requirement. A major advantage of optics resides in the fact that a "light pipe" can conduct both forward and backwards at the same time, i.e. a "light circuit" can be achieved without a circular path. An embodiment exploiting this behavior of light is shown in FIG. 19. A light source 337, photodetector 338 and prism 339 are optically linked by a single light pipe 340 which in turn may be optionally provided with an optical cladding 341. Optical couplers 342 and 343 are used to link the light source 337 and photodetector 338 with the light pipe 340.

The source coupler 342 is shown as injecting light at a higher point and angled away from the detector coupler 343 to prevent cross-talk between the couplers. A housing 344 and the cladding 341 serve to optically and physically insulate the light path. Light from the source 337 passes up the coupler 342 and light pipe 340 to the prism 339 where it must make two reflections (as in the preferred embodiment) in order to return back down the light pipe 340, out the coupler 343 and back to the detector 338. Some fraction of the reflected light that comes back down towards the detector will be lost down the source coupler 342.

The amount of light that is lost in the FIG. 19 embodiment will be a stable fraction of the total amount that is reflected down the light pipe 340 and can be safely ignored. In this embodiment the light pipe 340 and cladding 341 are shown passing through a header 345 which in turn is sealed into a suitably sized orifice in the vessel 346 that contains the medium 347 that is being tested. A major advantage of this device is that the light pipe 340 can be all or part of an extended optical fiber which would allow the electro-optics to be remotely located from the vessel 346 which could then be placed in an environment (such as extreme temperature) that the electro-optics could not withstand. As in the previous embodiments, a reference detector 348 can be used to cancel out variations in light source 337 output due to aging, temperature, variations in power supply, etc.

Use of reflections near the angle of total internal reflection serves to maximize the sensitivity to small changes in index of refraction that can arise from changes in medium density, temperature, chemical composition and or physical state. Prism materials can consist of any of a number of glasses (such as crown, BK 7, fused quartz etc.) or plastics (such as polycarb). In the embodiment of FIG. 17C, the medium becomes the prism and the block of material containing the prism defining cavity need only have a suitably high dielectric constant and need not even be transparent. In the most similar application (see Optek Inc. application note from a 1989, 1990 Data book), two reflections are used in a prism that are in total internal reflection in a gas (air) and in almost complete refraction in a tested liquid (such as water). When the prism is immersed in the liquid, the amount of light making both reflections is abruptly and substantially reduced. In this manner the prism functions as a detector for the presence or non presence of liquid as opposed to gas or vacuum. No effort is made to monitor changes in index of refraction in the gas or liquid.

Figure 18A:
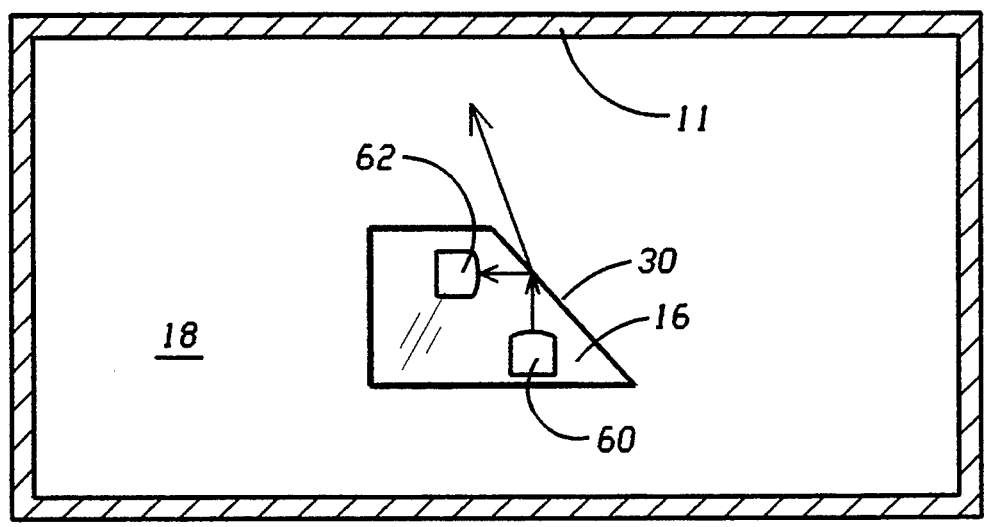
FIGS. 18A–18C illustrate additional alternate prism and radiation source configurations.
Figure 18B:
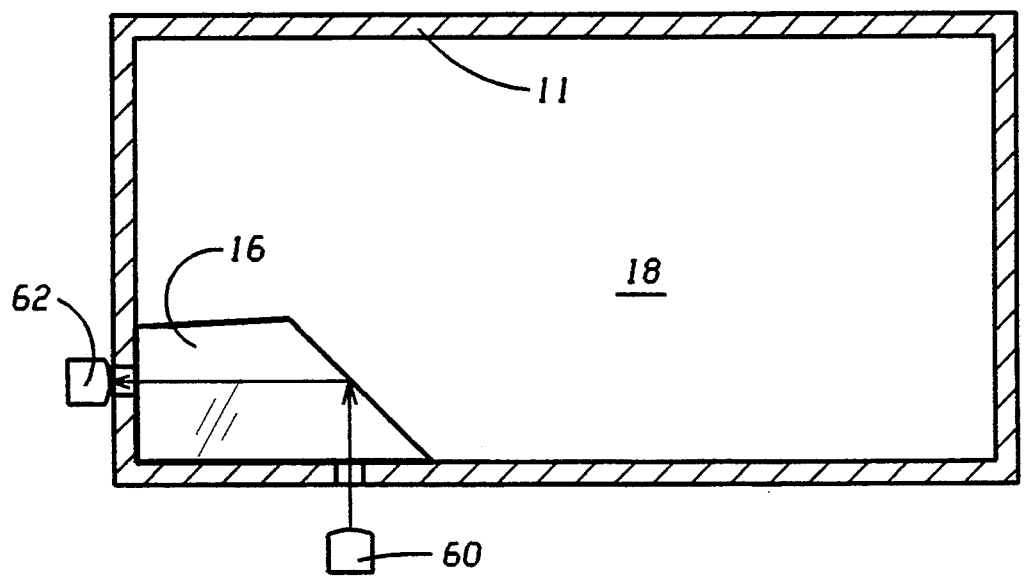
Figure 18C:
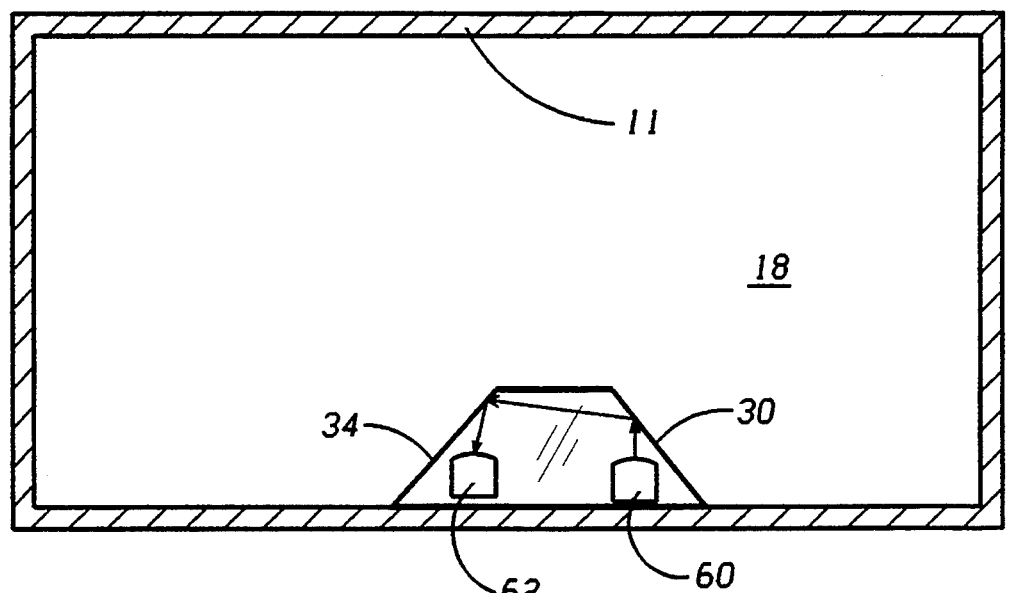

Multiple alternate embodiments of the invention are disclosed in FIGS. 18A, 18B and 18C. In FIG. 18A, both the light-emitting diode 60' and photodiode 62' are supported within a prism 16'. A single reflecting surface 30' is in contact with a gas within a vessel interior 18' of FIG. 18A and a second reflecting surface 341 is in contact with the gas in FIG. 18C.

In FIG. 18B, the vessel 11' supports a multi-faceted prism 16". A single reflecting surface 30" directs light to a photodetector 62". FIG. 18C is similar to the FIG. 18A embodiment except that two reflecting surfaces 30', 34' intercept the light beam as it travels from the light-emitting diode to the detector.

Figure 21:
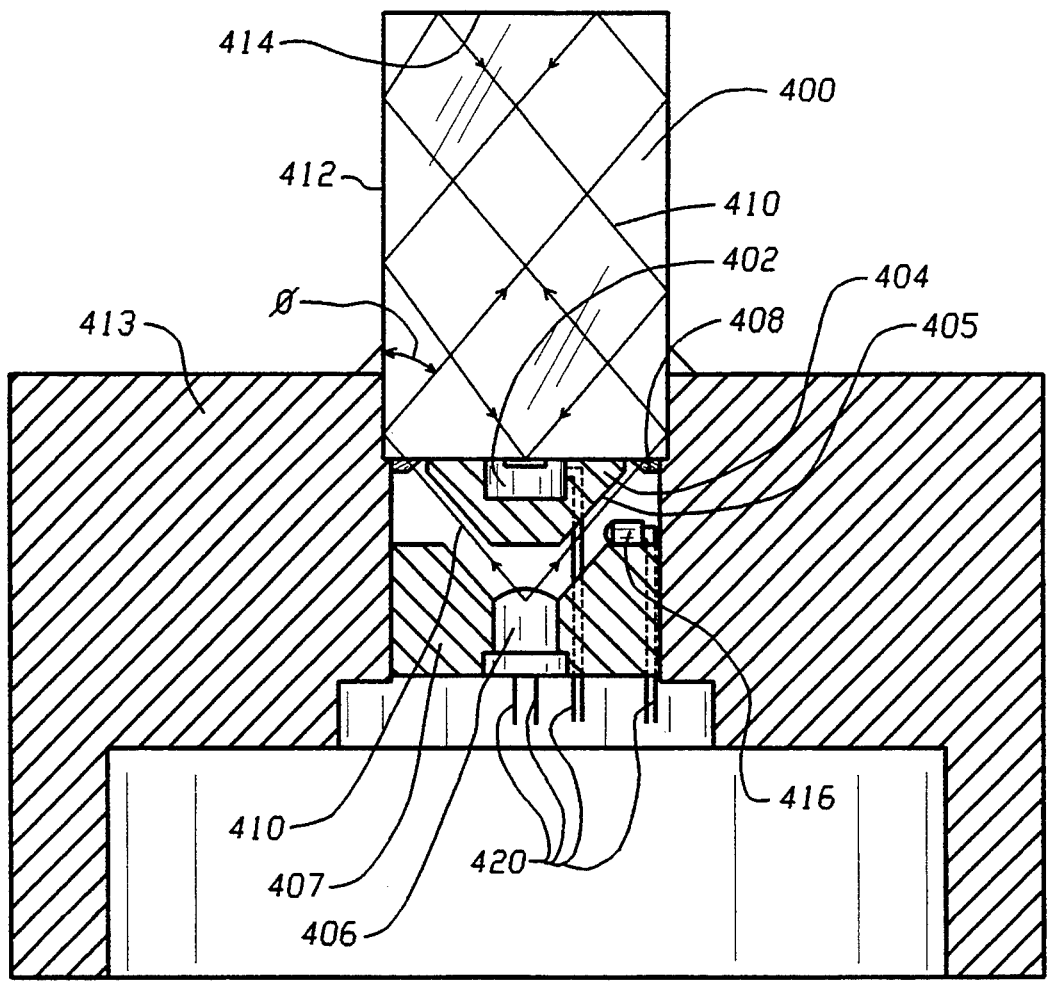
FIG. 21 is an alternate embodiment of the invention that incorporates a glass rod rather than a multifaceted prism as a means for determining index of refraction of a fluid in contact with the rod.
Figure 22:
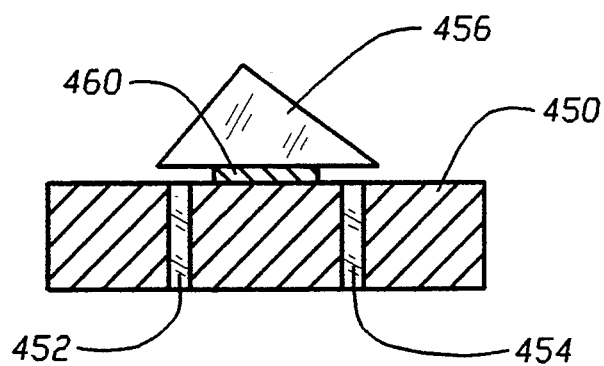
FIG. 22 is a section view showing an alternate means of mounting a prism in a vessel.

Referring to FIG. 21, a cylindrical rod 400 of optically transmissive material (such as glass) replaces the prism of the previous embodiments. Art optical detector 402 backed by an aperture stop 404 is situated at a low pressure (or non-immersed) end of the rod 400 so that a receptive portion of the detector 402 faces one end of the rod.

An optical source 406 supported by an insert 407 is situated below the aperture stop 404 and is oriented to direct radiation along an angled or beveled surface 405 of the aperture stop 404 through a ring lens 408 and into the rod 400. The diameter of the aperture stop 404, the shape of the lens 408, and the lens' location relative to the end of the rod as well as the location of the source 406 are controlled to allow only large angle rays 410 to enter the rod 400.

The angles of rays that are accepted into the rod 400 are constrained by the controlled parameters to be less than or equal to the angle of total reflection $\theta$ between the cylindrical outer surface 412 of the rod and the medium within a vessel 413 that supports the rod. This angle of total reflection is of course dependant on the index of refraction of the test medium which is the index of refraction R at the condition of interest, i.e, a given density or composition.

Rays that would strike the surface 412 at angles greater than the angle of total reflection $\theta$ are stopped by the aperture stop 404. Rays that are at or below the angle of total reflection will be totally or partially reflected each time they strike the outer surface of the rod.

By making multiple reflections the rays 410 that enter the rod 400 will eventually reach a far end of the rod where they are reflected by a reflective coating 414 applied to the far or distal end of the rod. The rays will then reflect off the coating 414 and reflect back down the rod. A certain percentage or proportion of the rays 410 that are emitted to enter the rod will strike the detector having made multiple reflections at the medium/rod interface.

Rays that are only partially reflected at this interface will be substantially attenuated if they make multiple reflections. The rays in total reflection will suffer little attenuation as they reflect off the cylindrical wall of the rod. When the condition of the medium that contact the rode changes (for example when the gas density changes) to cause the index of refraction of the medium to fall below R, rays close to the angle of total reflection will begin to go into total reflection and the light signal reaching the detector 402 will increase. As the index of refraction continues to drop a progressively greater fraction of rays will go into total reflection resulting in an even great light signal.

The rod and detector/source assembly are supported by the vessel 413 containing the medium for testing. FIG. 21 also uses a reference detector 416 mounted relative to the source 406 for use in eliminating source or detector response variations from the determination of the medium composition. Suitable electrical signals for activating the source 406, and responsive to the detector 402 and detector 416 are transmitted by conductors 420.

FIGS. 22, 23, 23A, 24 and 24A depict an alternate means of positioning a prism with respect to a vessel wall 450. The vessel depicted in FIG. 22 has two ports 452, 454 that are filled with a glass and direct light to a prism 456. The prism is attached to the vessel wall 450 by means of a glass preform 460. The preform 460 is a generally square (in plan) support made of a powdered glass molded to shape with a volatile binder. A preferred powdered glass is Corning 1990 which softens at around 500° C. The prism 456 is made of a higher softening point glass such as Crown Glass which softens around 730° C. When raised to a temperature above 500° C., the preform 460 fuses the prism 456 to the vessel wall to secure the prism 456 in place.

Figure 23:
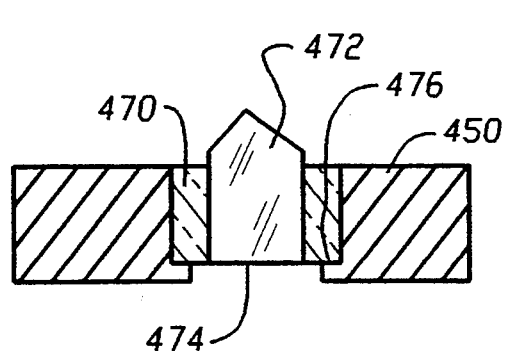
FIGS. 23 and 23A are section and plan views of a means of mounting a prism using a glass preform that supports the prism.
Figure 23A:
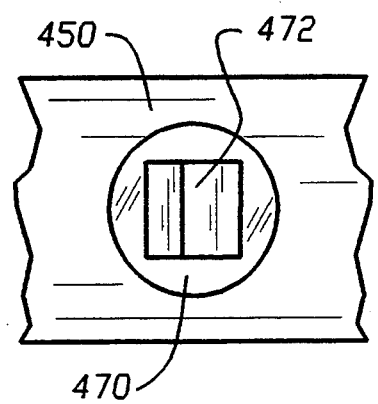
Figure 24:
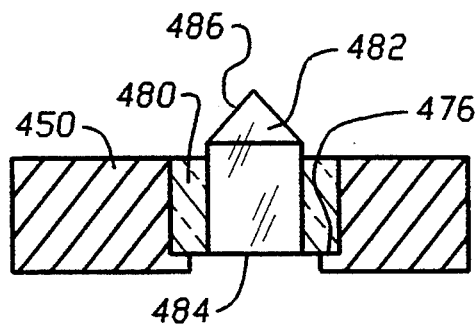
FIGS. 24 and 24A are section and plan views of a means of supporting a conical prism within a vessel.
Figure 24A:
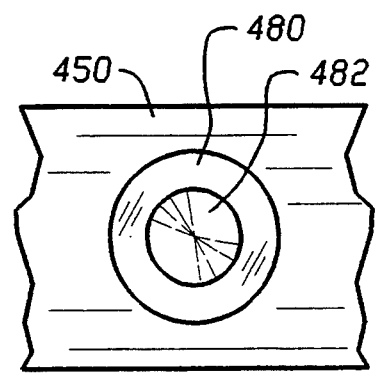

In FIGS. 23 and 24, two preforms 470, 480 support prisms 472, 482 that seat against a shoulder 476 of the wall 450. When fused, the preform and prism extend into the cavity in the wall and have exposed surfaces 474, 484 outside the vessel. Note, the prism 482 is a cylinder having a cone-shaped end 486 exposed to a medium inside the vessel interior.

While a preferred embodiment of the invention has been described with a degree of particularity, it is the intent that the invention include all modifications from the disclosed design falling within the spirit of scope of the appended claims.

We claim:

1. Sensor apparatus for monitoring the composition of a fluid comprising:
  a) a vessel for holding a fluid and including one or more openings for allowing radiation to enter and to exit the vessel;
  b) a radiation source for directing a beam of radiation along a path that causes the radiation to enter the vessel;
  c) a prism having a radiation transmitting surface that covers said one or more openings in the vessel and further having first and second reflecting surfaces having a specified orientation with respect to each other wherein a first reflecting surface is oriented with respect to an angle of incidence of radiation passing through the prism from the radiation source so that a significant portion of light contacting the first reflecting surface is reflected off the first reflecting surface along a path completely within the prism to the second reflecting surface where a significant portion of the radiation reaching the second reflecting surface is reflected off the second reflecting surface and exits the prism and the vessel;
  d) a first radiation detector for monitoring intensity of radiation leaving the vessel that has been reflected off the second reflecting surface of the prism;
  e) a second radiation detector for monitoring intensity of radiation from the radiation source that does not enter the vessel; and
  f) means for determining fluid composition based on the intensity sensed by the first and the second radiation detectors.

2. The sensor apparatus of claim 1 wherein the means for determining the fluid composition determines the fluid sample composition based upon a ratio of intensities sensed by the first and second radiation detectors.

3. The sensor apparatus of claim 1 where the source is an infrared light-emitting diode.

4. The sensor apparatus of claim 1 wherein the first reflecting surface is oriented with respect to an angle of incidence of radiation from the source so that a significant portion of light contacting the first reflecting surface is reflected and a significant portion is refracted when the fluid sample composition is near a composition of interest.

5. The sensor apparatus of claim 1 wherein the vessel has an entrance opening near the source for transmitting the radiation into the vessel and further has an exit opening for allowing radiation reflected off from the first and second surfaces to exit the vessel and impinge upon the first detector.

6. The sensor apparatus of claim 5 wherein the entrance and exit openings of said vessel are filled with a light transmissive material.

7. The sensor apparatus of claim 2 additionally comprising intensity control circuitry for activating the radiation source and wherein an output from the second radiation detector is used as a control input for the intensity control circuity to increase and decrease output from the radiation source.

8. The sensor apparatus of claim 1 wherein the sensor apparatus monitors a density of a gas within the vessel.

9. A method for determining the density of a gas comprising the steps of:
   a) mounting a prism in a vessel so that first and second reflecting surfaces of the prism that have a specific orientation with respect to each other are in contact with a gas inside the vessel interior and the prism covers one or more access openings in said vessel;
   b) directing radiation into one of the access openings to pass through a radiation transmitting surface of the prism along a path that causes at least some of the radiation to pass through the prism and reflect off the first reflecting surface to a path completely within the prism to the second reflecting surface where said radiation is again reflected toward one of said access openings to exit the vessel;
   c) monitoring radiation leaving the prism that has reflected off the first and second reflecting surfaces; and
   d) correlating monitored radiation with a density of gas inside the vessel.

10. The method of claim 9 wherein the step of directing radiation into the prism is performed by positioning a radiation source to direct radiation through the prism transmitting surface substantially normal to a radiation path.

11. The method of claim 10 comprising the additional step of monitoring radiation intensity from the radiation source that does not enter the vessel in addition to monitoring radiation intensity of the radiation that enters and exits the prism and wherein the step of correlating monitored radiation intensity with fluid density is performed by taking a ratio of intensities of radiation that does and does not pass through the prism.

12. Apparatus for monitoring a density of a gas comprising:
   a) a vessel containing a gas whose density is being monitored, said vessel including a gas port for putting gas into the vessel and at least one optics port for allowing radiation to enter and/or leave the vessel;
   b) multi-sided radiation transmissive prism supported within the vessel to intercept radiation entering the vessel having first and second reflecting surfaces at an interface between the gas and the radiation transmissive prism;
   c) a radiation source for directing a beam of radiation into the vessel through the optics port to the radiation transmissive means along a path causing the radiation to strike a first reflecting surface of said prism at a controlled angle and then reflect off said first reflecting surface and pass along a path completely within the prism to said second reflecting surface;
   d) a detector for monitoring radiation intensity after the radiation reflects off the second reflecting surface of said prism; and
   e) circuitry for providing an indication of gas density based upon an output from the detector.

13. The apparatus of claim 12 where the circuitry provides a two-state output signal indicating whether gas density within the vessel is above or below a specified gas density.

14. A sensor for monitoring the composition of a fluid comprising:
   a) a vessel for holding a fluid within a confined region;
   b) an elongated radiation transmissive rod having a reflecting surface at a distal end and a generally cylindrical outer surface in contact with the fluid within said vessel symmetric with respect to a centerline of the rod that extends along at least a portion of the length of the rod;
   c) a radiation source positioned along a line co-incident with the centerline of said rod for emitting radiation toward a proximal, non-immersed end of the elongated rod;
   d) an aperture stop positioned between the radiation source and the proximal end of the rod that includes a surface for intercepting radiation from the source to allow said radiation to enter the proximal end of said elongated rod at only controlled angles;
   e) a first radiation detector mounted to the aperture stop for monitoring intensity of radiation that has reflected off the reflecting surface of the rod;
   f) a second radiation detector located behind the aperture stop for monitoring intensity of radiation from the radiation source that does not enter the elongated rod; and
   g) means for determining fluid composition based on the intensity sensed by the first and the second radiation detectors.

15. The sensor of claim 14 wherein the first radiation detector is positioned near the proximal end of the rod opposite the reflecting surface and is positioned within a cavity in the aperture stop.

16. Sensor apparatus for monitoring the composition of a fluid comprising:
   a) a prism positioned with a fluid sample and having a refracting surface in contact with a fluid sample;
   b) a radiation source for directing a beam of radiation along a path that causes the radiation to reach the refracting surface of the prism at an angle to a normal direction of the surface to cause a substantial portion of the radiation to be refracted away from the normal to pass through the refracting surface and enter said fluid;
   c) a first radiation detector for monitoring intensity of radiation that has been refracted at the refracting surface of the prism and enters the fluid sample; and
   d) circuitry for determining fluid composition based on the radiation intensity sensed by the first radiation detector.

* * * * *